United States Patent
Cahoon et al.

(10) Patent No.: US 8,461,322 B2
(45) Date of Patent: Jun. 11, 2013

(54) PLANT 1-DEOXY-D-XYLULOSE 5-PHOSPHATE REDUCTOISOMERASE

(75) Inventors: Rebecca E. Cahoon, Lincoln, NE (US); Yong Tao, Newark, DE (US)

(73) Assignee: E I du Pont de Nemours and Company, Wilmington, DE (US)

(*) Notice: Subject to any disclaimer, the term of this patent is extended or adjusted under 35 U.S.C. 154(b) by 409 days.

(21) Appl. No.: 12/938,393

(22) Filed: Nov. 3, 2010

(65) Prior Publication Data
US 2011/0185450 A1  Jul. 28, 2011

Related U.S. Application Data

(60) Division of application No. 11/895,093, filed on Aug. 23, 2007, now Pat. No. 7,842,855, which is a division of application No. 11/363,798, filed on Feb. 28, 2006, now Pat. No. 7,282,359, which is a continuation-in-part of application No. 09/857,557, filed as application No. PCT/US99/28616 on Dec. 3, 1999, now abandoned.

(60) Provisional application No. 60/110,865, filed on Dec. 4, 1998.

(51) Int. Cl.
*C12N 15/29* (2006.01)
*C12N 15/52* (2006.01)
*C12N 15/82* (2006.01)
*A01H 5/00* (2006.01)
*A01H 5/10* (2006.01)

(52) U.S. Cl.
USPC ......... 536/23.6; 536/23.2; 800/298; 435/183; 435/320.1; 435/419

(58) Field of Classification Search
None
See application file for complete search history.

(56) References Cited

U.S. PATENT DOCUMENTS

| | | |
|---|---|---|
| 2004/0031072 A1 | 2/2004 | La Rosa et al. |
| 2004/0034888 A1 | 2/2004 | Liu et al. |

FOREIGN PATENT DOCUMENTS

| | | |
|---|---|---|
| EP | 1586652 | 10/2005 |
| WO | WO 97/12982 | 4/1997 |
| WO | WO 00/34448 | 6/2000 |

OTHER PUBLICATIONS

Schwender, J. et al. FEBS Letters (1999), vol. 455: 140-144. Cloning and heterologous expression of a cDNA encoding 1-deoxy-D-xylulose 5-hosphate reductoisomerase of *Arabidopsis thaliana*.*
Tomohisa Kuzuyama et al., Tetrahedron letters, vol. 39:7913-7916, 1998, Fosmidomycin, a specific inhiitor of 1-Deoxy-D-Xylulose 5-Phosphate Reductoisomerase in the Nonmevalonate Pathway for Terpenoid biosynthesis.
EMBL Sequence Data Library Accession No. AA753357, Jan. 21, 1998, B. H. Nahm et al., Large-scale sequencing analysis of ESTs from rice immature seed.
Shunji Takahashi et al., PNAS, vol. 95:9879-9884, 1998, A 1-deoxy-D-xylulose 5-phosphate reductoisomerase catalyzing the formation of 2-C-methyl-D-erythritol 4-phosphate in an alternative nonmevalonate pathway for terpenoid biosynthesis.
Jorg Schwender et al., FEBS Letters, vol. 455:140-144, 1999, Cloning and heterologous expression of a cDNA encoding 1-deoxy-D-xylulose-5-phosphate reductoisomerase of *Arabidopsis thaliana*.
B. Markus Lange et al., Archives of Biochem. & Biophys., vol. 365(1):170-174, 1999, Isoprenoid biosynthesis via a Mevalonate-Independent pathway in Plants: Cloning and Heterologous Expression of 1-Deoxy-D-xylulose5-phosphate Reductoisomerase from Peppermint.
National Center for Biotechnology Information General Identifier No. 1001556, Jul. 4, 2001, T. Kaneko et al., Sequence analysis of the genome of the unicellular cyanobacterium *Synechocystis* sp. strain PCC6803. I. sequence features in the 1 Mb region from map positions 64% to 92% of the genome.
Takakazu Kaneko et al., DNA Res., vol. 2:153-166, 1995, Sequence analysis of the genome of the unicellular cyanobacterium *Synechocystis* sp. strain PCC6803. I. sequence features in the Mb region from the map positions 64% to 92% of the genome.
Takakazu Kaneko et al., DNA Res., vol. 3:109-136, 1996, Sequence Analysis of the Genome of the Unicellular Cyanobacterium *Synechocystis* sp. Strain PCC6803. II. Sequence Determination of the Entire Genome and Assignment of Potential Protein-coding Regions.
National Center for Biotechnology Information General Identifier No. 3434984, Feb. 6, 1999, T. Kuzuyama.
National Center for Biotechnoloogy Information General Identifier No. 4886307, Aug. 25, 1999, J. Schwender et al., Cloning and heterologous expression of a cDNA encoding 1-deoxy-D-xylulose-5-phosphate reductoisomerase of *Arabidopsis thaliana*.
National Center for Biotechnology Information General Identifier No. 4581856, Apr. 28, 1999, B. M. Lange et al., Isoprenoid biosynthesis via a mevalonate-independent pathway in plants: cloning and heterologous expression of 1-deoxy-D-xylulose-5-phosphate reductoisomerase from peppermint.
National Center for Biotechnology Information General Identifier No. 2496789, Aug. 20, 2001, T. Kaneko et al., Sequence analysis of the genome of the unicellular cyanobacterium *Synechocystis* sp. strain PCCC6803. I. Sequence features in the 1 Mb region from the map positions 64% to 92% of the genome.
Tomohisa Kuzuyama et al., Tetrahedron Letters, vol. 39:4509-4512, 1998, Direct Formation of 2-C-Methyl-D-Erythritol 4-Phosphate from 1-Deoxy-D-Xylulose 5-Phosphate by 1-Deoxy-D-Xylulose 5-Phosphate Reductoisomerase, a New Enzyme in the Non-Mevalonate Pathway to isopentenyl Diphosphate.

* cited by examiner

*Primary Examiner* — Russell Kallis

(57) ABSTRACT

This invention relates to an isolated nucleic acid fragment encoding a 1-deoxy-D-xylulose 5-phosphate reductoisomerase. The invention also relates to the construction of a chimeric gene encoding all or a portion of the 1-deoxy-D-xylulose 5-phosphate reductoisomerase, in sense or antisense orientation, wherein expression of the chimeric gene results in production of altered levels of the 1-deoxy-D-xylulose 5-phosphate reductoisomerase in a transformed host cell.

15 Claims, 3 Drawing Sheets

FIG. 1A

```
SEQ ID NO:6    1 MALKVVSFPGDLAAVSFLDSNRGGAF----NQLKVDLPFQTRDRRAVSLRRTCCSMQQAP
SEQ ID NO:16   1 MAALKASFRGELSAASFLDSSRG-PL----VQHKVDFTFQRKGKRAISLRRTCCSMQQAP
SEQ ID NO:18   1 MMALNISSPAEVKSIFFADSFKSNCLTAK--FSGGFAFKKERRAASGGRVYCSVQATP
SEQ ID NO:20   1 TS----SFSLLELSSGTTRSRRGAAFRPRQHQRKVDLTFQRRDKRAAYLR-TCCSMQQGP
SEQ ID NO:21   1 AP-----------------------------------------------------------
SEQ ID NO:24   1 MA-LNLPSPAQVKPLFFSSN-------NSTKLPGSFSLKRKDSDTTVERRVYCSAAAQS
SEQ ID NO:25   1 MA------PTEIKTLSFLDSSKSN-YNLNPLKFQGGFAFKRKDSGCTAAKRVHCSAQSQS  60
                                  *   *  ****       *      *  *  *******

SEQ ID NO:6   57 PP-AWPGRAVVEPGR-RSWDGPKPISIVGSTGSIGTQTLDIVAENPDKFRVVALAAGSNV
SEQ ID NO:16  56 PP-AWPGRAVAEPGR-RSWDGPKPISIVGSTGSIGTQTLDIVAENPDKFRVVALAAGSNV
SEQ ID NO:18  58 PPPAWPGRAVPEQGR-KTWDGPKPISIVGSTGSIGTQTLDIVAENPDKFKVVALAAGSNV
SEQ ID NO:20  56 PP-AWPGRAVAEPER-RSWEGPKPISIVGSTGSIGTQTLDIVAENPDKFRVVALAAGSNV
SEQ ID NO:21   3 ---------R-QSWDGPKTWDGQKPISIVGSTGSIGTQTLSIVAEFPERFKVVSLAAGSNI
SEQ ID NO:24  52 PPPAWPGTAIPEPSDFKTWDGQKPISIVGSIGTQTLSIVAEFPERFKVVSLAAGSNI
SEQ ID NO:25  54 PPPAWPGRAFPEPGR-MTWEGPKPISVIGSTGSIGTQTLDIVAENPDKFRIVALAAGSNV  120
                 *  ****   * **   * * **** * **** ******* *****  ** ********

SEQ ID NO:6  115 TLLADQVKTFKPKLVAVRNESLVDELKEALADCCDWKPEIIPGEQGVIEVARHPDAVTVVT
SEQ ID NO:16 114 TLLADQVKTFKPKLVAVRNESLVDELKEALADCEEKPEIIPGEQGVIEVARHPDAVTVVT
SEQ ID NO:18 117 TLLADQVKREKPQLVAVRNESLIAELHDVEEKPEIIPGEQGIIEVARHPDAVSVVT
SEQ ID NO:20 114 TLLADQVKTFKPKLVAVRNESLLNELKEALAGCEEMPEIIPGEQGVIEVARHPDAVTVVT
SEQ ID NO:21  48 TLLADQVRRFKPALVAVRNESLINELKEALADLDYKLEIIPGEQGVIEVARHPEAVTVVT
SEQ ID NO:24 112 TLLADQIKTFKPEVVGLRNESLIDELKEALADVDHKPEIIPGEQGVIEAARHPDATTVVT
SEQ ID NO:25 113 TLLADQVKAFKPKLVSVKDESLISELKEALAGFEDMPEIIPGEQMIEVARHPDAVTVVT  180
                 ******    **   * ***    *  *****       ******  ** **** *   ***
```

FIG. 1B

```
SEQ ID NO:6   175 GIVGCAGLKPTVAAIEAGKDIALANKETLIAGGPFVLPLAQKHHKVKILPADSEHSAIFQC
SEQ ID NO:16  174 GIVGCAGLKPTVAAIEAGKDIALANKETLIAGGPFVLPLAHKHKVKILPADSEHSAIFQC
SEQ ID NO:18  177 GIVGCAGLKPTVAAIEAGKDIALANKETLIAGGPFVLPLAQKHNVKILPADSEHSAIFQC
SEQ ID NO:20  174 GIVGCAGLKPTVAAIEAGKDIALANKETLIAGGPFVLPLAHKHNVKILPADSEHSAIFQC
SEQ ID NO:21  108 GIVGCAGLKPTVAAIEAGKDIALANKETLIAGGPFVLPLANKHNVKILPADSEHSAIFQC
SEQ ID NO:24  172 GIVGCAGLKPTVAAIEAGKDIALANKETMIAGAPFVLPLAHKHNIKILPADSEHSAIFQS
SEQ ID NO:25  173 GIVGCAGLKPTVAAIEAGKDIALANKETLIAGGPFVLPLAKKHNVKILPADSEHSAIFQC
                  181                                                        240

SEQ ID NO:6   235 IQGLPEGALRRIILTASGGAFRDWPVDKLKEVKVADALKHPNWNMGKKITVDSATLFNKG
SEQ ID NO:16  234 IQGLSEGALRRIILTASGGAFRDWPVDRLKDVKVADALKHPNWNMGRKITVDSATLFNKG
SEQ ID NO:18  237 IQGLPEGALRRVILTASGGAFRDWPVDKLKDVKVKVADALKHPNWNMCKKITVDSATLFNKG
SEQ ID NO:20  234 IQGLSEGSLRRVILTASGGAFRDWPVEKLKDVKVKVADALKHPNWSMGKKITVDSATLFNKG
SEQ ID NO:21  168 IQGLPEGALRKIILTGSGGAFRDWPVEKLKEVKVADALKHPNWNMGKKITVDSATLFNKG
SEQ ID NO:24  232 IQGLPKGALRKILTASGGAFREWPAEKMKDIKLADALKHPIWSLGRKITIDSATLFNKG
SEQ ID NO:25  233 IQGLPEGALRRIILTASGGAFRDLPVEKLKEVKVADALKHPNWNMGKKITVDSATLFNKG
                  241                                                        300

SEQ ID NO:6   295 LEVIEAHYLFGAEYDDIEIVIHPQSIIHSMIETQDSSVLAQLGWPDMRIPTLYTMSWPDR
SEQ ID NO:16  294 LEVIEAHYLFGAEYDDIEIVIHPQSIIHSMIETQDSSVLAQLGWPDMRLPILYLSWPDR
SEQ ID NO:18  297 LEVIEAHYLFGADYDHIEIVIHPQSIIHSMIETQDSSVLAQLGWPDMRLPILYLSWPDR
SEQ ID NO:20  294 LEVIEAHYLFGAEYDDIEIVIHPQSIIHSMIETQDSSVLAQLGWPDMRLPILYLSWPDR
SEQ ID NO:21  228 LEVIEAHYLFGASYDDIEIVIHPQSIIHSLVETQDSSVIAQLGIPDMRLPLLYLSWPER
SEQ ID NO:24  292 LEVIEAHYLFGAEYDDIEIVIHPQSIIHSMVETQDSSVLAQLGWPDMRLPILYTLSWPER
SEQ ID NO:25  293 LEVIEAHYLFGAEYDDIEIVIHPQSIIHSMVETQDSSVLAQLGWPDMRLPILYTLSWPER
                  301                                                        360
```

FIG. 1C

```
                     ***  *********          *  ***   *********************
SEQ ID NO:6    355  IYCSEVTWPRLDLCKLGSLTFKAPDNVKYPSMDLAYAAGRAGGTMTGVLSAANEKAVELF
SEQ ID NO:16   354  IYCSEVTWPRLDLCKLGSLTFRAPDNVKYPSMDLAYAAGRAGGTMTGVLSAANEKAVELF
SEQ ID NO:18   357  IYCSEVTWPRLDLCKLGSLTFKTPDNVKYPSMNLAFSAGRAGGTMTGVLSAANEKAVEMF
SEQ ID NO:20   354  VYCSEVTWPRLDLCKLGSLTFKAPDNVKYPSVDLAYAAGRAGGTMTGVLSAANEKAVELF
SEQ ID NO:21   288  VPCSEVTWPRLDLCKLGSLTFKKPDNVKYPSMDLAYAAGRAGGTMTGVLSAANEKAVEMF
SEQ ID NO:24   352  IYCSEVTWPRLDLSKYGSLTFYAPDDKKFPSVNLCYAAGRAGGTMTGVLSAANEKAVEMF
SEQ ID NO:25   353  IYCSEITWPRLDLCKVD-LTFKKPDNVKYPSMDLAYAAGRAGGTMTGVLSAANEKAVEMF
                    361                                                        420

***  * **********  ***  ***  *****   ***           **
SEQ ID NO:6    415  IDEKIGYLDIFKVVELTCDAHRNELVTRPSLEEIIHYDLWAREYAASLQPST-GLSPVPV  473
SEQ ID NO:16   414  IDEKISYLDIFKVVELTCNAHRNELVTSPSLEEIVHYDLWARRYAASLQPSS-GLSPVPA  472
SEQ ID NO:18   417  IDEKISYWNLEKVVELTCEKHQNELVSSPSLEEIIHYDLWARKYAASLQ-DSSSFTPILA  475
SEQ ID NO:20   414  IDEKISYLDIFKVVEMTCDAHRNELVTRPSLEEIIHYDQWARKFAANLQPSSGRSPVLA   473
SEQ ID NO:21   348  IDEKISYLDIFKVVELTCDKHRNELVTSPSLEEIVHYDLWAREYAANVQLSS-GARPVHA  406
SEQ ID NO:24   412  VEEKISYLDIFKVVELTCQEHQKELVASPSLEEIIHYDQWARQYAASLQKASS------V  465
SEQ ID NO:25   412  IDEKIGYLDIFKVVELTCDKHRSEMAVSPSLEEIVHYDQWARDYAATV-LKSAGLSPALV  470
                    421                                                        480
```

PLANT 1-DEOXY-D-XYLULOSE 5-PHOSPHATE REDUCTOISOMERASE

This application is a divisional of U.S. Application No. 11/895,093, filed Aug. 23, 2007, now U.S. Pat. No. 7,842,855, and herein incorporated by reference, which is a divisional of U.S. application Ser. No. 11/363,798, filed Feb. 28, 2006, now U.S. Pat. No. 7,282,359, and herein incorporated by reference, which is a continuation in part of U.S. application Ser. No. 09/857,557, filed Jun. 4, 2001, now abandoned and herein incorporated by reference, which is a 35 U.S.C. 371 national filing of International Application No. PCT/US99/28616, filed Dec. 3, 1999, which claims the benefit of U.S. Provisional Application No. 60/110,865, filed Dec. 4, 1998.

FIELD OF THE INVENTION

This invention is in the field of plant molecular biology. More specifically, this invention pertains to nucleic acid fragments encoding 1-deoxy-D-xylulose 5-phosphate reductoisomerase in plants and seeds.

BACKGROUND OF THE INVENTION

Isoprenoids comprise the largest family of natural products, including numerous secondary compounds which play different functional roles in plants as hormones, photosynthetic pigments, electron carriers, and structural components of membranes. The fundamental unit in isoprenoid biosynthesis, isopentenyl diphosphate (IPP), is normally synthesized by the condensation of acetyl CoA through the mevalonate pathway. In many organisms including several bacteria, algae and plant plastids, IPP is synthesized by a mevalonate-independent pathway. The initial step in this pathway is the condensation of pyruvate and glyceraldehyde 3-phosphate to form 1-deoxy-D-xylulose 4-phosphate. In the committed step towards IPP formation 1-deoxy-D-xylulose 5-phosphate reductoisomerase catalyzes in a single step an intramolecular rearrangement and reduction of 1-deoxy-D-xylulose 4-phosphate to form 2-C-methyl-D-erythritol 4-phosphate.

The *E. coli* 1-deoxy-D-xylulose 5-phosphate reductoisomerase enzyme has only recently been identified. Comparison of the amino acid sequence of the *E. coli* 1-deoxy-D-xylulose 5-phosphate reductoisomerase with those of *Bacillus subtilis, Haemophilus influenzae, Helicobacter pyroli, Mycobacterium tuberculosis* and *Synechocystis* sp. PCC6803 showed that there is little conservation among these sequences (Takahashi et al. (1998) *Proc. Natl. Acad. Sci. USA* 95:9879-9884).

SUMMARY OF THE INVENTION

The present invention concerns isolated polynucleotides comprising a nucleotide sequence encoding a polypeptide having 1-deoxy-D-xylulose 5-phosphate reductoisomerase activity. wherein the amino acid sequence of the polypeptide and the amino acid sequence of SEQ ID NO:6, 8, 16, 18, 20 or 24 have at least 93% sequence identity. It is preferred that the identity be at least 95%, it is more preferred that the identity be at least 98%. The present invention also relates to isolated polynucleotides comprising the complement of the nucleotide sequence. More specifically, the present invention concerns isolated polynucleotides encoding the polypeptide sequence of SEQ ID NO:6, 8, 16, 18, 20 or 24 or nucleotide sequences comprising the nucleotide sequence of SEQ ID NO:5, 7, 15, 17, 19 or 23.

In a first embodiment, the present invention includes an isolated polynucleotide comprising: (a) a nucleotide sequence encoding a polypeptide having 1-deoxy-D-xylulose 5-phosphate reductoisomerase activity, wherein the polypeptide has an amino acid sequence of at least 93%, 95% or 98% sequence identity, based on the Clustal V method of alignment, when compared to one of SEQ ID NO:6, 8, 16, 18, 20 or 24, or (b) a complement of the nucleotide sequence, wherein the complement and the nucleotide sequence consist of the same number of nucleotides and are 100% complementary. The polypeptide preferably comprises the amino acid sequence of SEQ ID NO:6, 8, 16, 18, 20 or 24. The nucleotide sequence preferably comprises the nucleotide sequence of SEQ ID NO:5, 7, 15, 17, 19 or 23.

In a second embodiment, the present invention concerns a recombinant DNA construct comprising any of the isolated polynucleotides of the present invention operably linked to at least one regulatory sequence, and a cell, a plant, and a seed comprising the recombinant DNA construct.

In a third embodiment, the present invention includes a vector comprising any of the isolated polynucleotides of the present invention.

In a fourth embodiment, the present invention concerns a method for transforming a cell comprising transforming a cell with any of the isolated polynucleotides of the present invention. The cell transformed by this method is also included. Advantageously, the cell is eukaryotic, e.g., a yeast or plant cell, or prokaryotic, e.g., a bacterium.

In a fifth embodiment, the present invention includes a method for producing a transgenic plant comprising transforming a plant cell with any of the isolated polynucleotides of the present invention and regenerating a plant from the transformed plant cell. The invention is also directed to the transgenic plant produced by this method, and seed obtained from this transgenic plant.

In a sixth embodiment, the present invention concerns an isolated polypeptide having 1-deoxy-D-xylulose 5-phosphate reductoisomerase activity, wherein the polypeptide has an amino acid sequence of at least 93%, 95% or 98% sequence identity, based on the Clustal V method of alignment, when compared to one of SEQ ID NO:6, 8, 16, 18, 20 or 24. The polypeptide preferably comprises one of SEQ ID NO:6, 8, 16, 18, 20 or 24.

In a seventh embodiment, the present invention includes to a method for isolating a polypeptide having 1-deoxy-D-xylulose 5-phosphate reductoisomerase activity comprising isolating the polypeptide from a cell or culture medium of the cell, wherein the cell comprises a recombinant DNA construct comprising a polynucleotide of the invention operably linked to at least one regulatory sequence.

In an eighth embodiment, this invention concerns a method for selecting a transformed cell comprising: (a) transforming a host cell with the recombinant DNA construct or an expression cassette of the present invention; and (b) growing the transformed host cell, preferably a plant cell, under conditions that allow expression of the 1-deoxy-D-xylulose 5-phosphate reductoisomerase polynucleotide in an amount sufficient to complement a null mutant in order to provide a positive selection means.

In a ninth embodiment, this invention concerns a method of altering the level of expression of a 1-deoxy-D-xylulose 5-phosphate reductoisomerase protein in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the 1-deoxy-D-xylulose 5-phosphate reductoisomerase protein in the transformed host cell.

A further embodiment of the instant invention is a method for evaluating at least one compound for its ability to inhibit the activity of a 1-deoxy-D-xylulose 5-phosphate reductoisomerase, the method comprising the steps of: (a) introducing into a host cell a recombinant DNA construct comprising a nucleic acid fragment encoding a 1-deoxy-D-xylulose 5-phosphate reductoisomerase polypeptide, operably linked to at least one regulatory sequence; (b) growing the host cell under conditions that are suitable for expression of the recombinant DNA construct wherein expression of the recombinant DNA construct results in production of 1-deoxy-D-xylulose 5-phosphate reductoisomerase polypeptide in the host cell; (c) optionally purifying the 1-deoxy-D-xylulose 5-phosphate reductoisomerase polypeptide expressed by recombinant DNA construct in the host cell; (d) treating the 1-deoxy-D-xylulose 5-phosphate reductoisomerase polypeptide with a test compound; (e) comparing the activity of the 1-deoxy-D-xylulose 5-phosphate reductoisomerase polypeptide that has been treated with the test compound to the activity of an untreated 1-deoxy-D-xylulose 5-phosphate reductoisomerase polypeptide, and (f) selecting compounds with potential for inhibitory activity based on the results of step (e) (preferably selecting the test compound if it has an inhibitory effect on the activity of 1-deoxy-D-xylulose 5-phosphate reductoisomerase based on said comparison of said step (e)).

BRIEF DESCRIPTION OF THE DRAWING AND SEQUENCE DESCRIPTIONS

The invention can be more fully understood from the following detailed description and the accompanying drawing and Sequence Listing which form a part of this application.

FIGS. 1A-1C show a comparison of the amino acid sequences of the 1-deoxy-D-xylulose 5-phosphate reductoisomerase polypeptides from the following: a rice clone, rlr6.pk0073.d5 (SEQ ID NO:6); a corn clone, p0004.cb1hh74r (SEQ ID NO:16); a soybean contig assembled from clones ses2w.pk0029.e5, sgc3c.pk001.d16, and sr1.pk0008.d1:fis (SEQ ID NO:18); a wheat clone, wlm12.pk0003.d11:fis (SEQ ID NO:20); *Arabidopsis thaliana* (NCBI General Identifier No. 4886307; SEQ ID NO:21); a soybean clone, sl2.pk125.m18:fis (SEQ ID NO:24); and *Mentha×piperita* (NCBI General Identifier No. 77378042; SEQ ID NO:25). Amino acids conserved among all sequences are indicated with an asterisk (*) on the top row; dashes are used by the program to maximize alignment of the sequences. Amino acid residues are numbered to the left of each sequence row and to the right of the last sequence row. Consensus amino acid residues are numbered below each section of sequence alignment.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825.

TABLE 1

1-Deoxy-D-Xylulose 5-Phosphate Reductoisomerase

| Plant | Clone Designation | SEQ ID NO: (Nucleotide) | SEQ ID NO: (Amino Acid) |
|---|---|---|---|
| Corn | Contig of:<br>p0004.cb1hh74r<br>p0012.cglac07r<br>p0006.cbyvo28r | 1 | 2 |
| Corn | Contig of:<br>cen3n.pk0157.e12<br>cr1n.pk0095.g3<br>cho1c.pk004.f12<br>csi1.pk0041.f11 | 3 | 4 |
| Rice | rlr6.pk0073.d5 | 5 | 6 |
| Soybean | Contig of:<br>sml1c.pk001.c15<br>sml1c.pk005.a24<br>sl1.pk0021.a6<br>sl2.pk124.p17<br>sl1.pk0036.a5<br>sl2.pk0111.c9<br>sl1.pk152.i19<br>sl2.pk0039.d4 | 7 | 8 |
| Soybean | Contig of:<br>sr1.pk0008.d1<br>sr1.pk0007.c11<br>srm.pk0014.f8 | 9 | 10 |
| Wheat | Contig of:<br>wlm12.pk0003.d11<br>wr1.pk0084.a4 | 11 | 12 |
| Wheat | Wlm24.pk0014.d7 | 13 | 14 |
| Corn | p0004.cb1hh74r | 15 | 16 |
| Soybean | Contig of:<br>ses2w.pk0029.e5<br>sgc3c.pk001.d16<br>sr1.pk0008.d1:fis | 17 | 18 |
| Wheat | wlm12.pk0003.d11:fis | 19 | 20 |
| Soybean | sl2.pk125.m18:fis | 23 | 24 |

SEQ ID NO:21 corresponds to NCBI General Identifier No. 4886307, which is the amino acid sequence of 1-deoxy-D-xylulose 5-phosphate reductoisomerase from *Arabidopsis thaliana* (Schwender et al. (1999) *FEBS Lett* 455:140-144).

SEQ ID NO:22 corresponds to NCBI General Identifier No. 4581856, which is the amino acid sequence of 1-deoxy-D-xylulose 5-phosphate reductoisomerase from *Mentha×piperita* (Lange et al. (1999) *Arch Biochem Biophys* 365:170-174).

SEQ ID NO:25 corresponds to NCBI General Identifier No. 77378042, which replaced NCBI General Identifier No. 4581856 on Oct. 7, 2005, as the amino acid sequence of 1-deoxy-D-xylulose 5-phosphate reductoisomerase from *Mentha×piperita*.

SEQ ID NO:26 corresponds to a "His-tag", a twenty amino acid polypeptide fragment that contains six consecutive histidine residues.

SEQ ID NO:27 corresponds to a His-tagged *E. coli* 1-deoxy-D-xylulose 5-phosphate reductoisomerase.

SEQ ID NO:28 corresponds to a His-tagged *Synechocystis* 1-deoxy-D-xylulose 5-phosphate reductoisomerase.

SEQ ID NO:29 corresponds to a full-length His-tagged rice 1-deoxy-D-xylulose 5-phosphate reductoisomerase.

SEQ ID NO:30 corresponds to a 442 amino acid truncated rice His-tagged 1-deoxy-D-xylulose 5-phosphate reductoisomerase.

SEQ ID NO:31 corresponds to a 418 amino acid truncated rice His-tagged 1-deoxy-D-xylulose 5-phosphate reductoisomerase.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides, of the nucleic acid sequence of the SEQ ID NOs:1, 3, 5, 7, 9, 11, 13, 15, 17, 19, and 23.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises any of the isolated polynucleotides of the present invention operably linked to at least one regulatory sequence.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

The "Clustal V method of alignment" corresponds to the alignment method labeled Clustal V (described by Higgins and Sharp (1989) *CABIOS.* 5:151-153) and found in the Megalign program of the LASERGENE bioinformatics computing suite (DNASTAR Inc., Madison, Wis.). The "default parameters" are the parameters pre-set by the manufacturer of the program and for multiple alignments they correspond to GAP PENALTY=10 and GAP LENGTH PENALTY=10, while for pairwise alignments they are KTUPLE 1, GAP PENALTY=3, WINDOW=5 and DIAGONALS SAVED=5. After alignment of the sequences, using the Clustal V program, it is possible to obtain a "percent identity" by viewing the "sequence distances" table on the same program.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs: 1, 3, 5, 7, 9, 11, 13, 15, 17, 19, and 23, and the complement of such nucleotide sequences may be used in methods of selecting an isolated polynucleotide that affects the expression of a polypeptide in a plant cell. A method of selecting an isolated polynucleotide that affects the level of expression of a polypeptide, such as 1-deoxy-D-xylulose 5-phosphate reductoisomerase in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 93, 94, 95, 96, 97, 98, 99 or 100% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) J. Mol. Biol. 215:403-410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70-73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

The present invention includes an isolated polynucleotide comprising a nucleotide sequence encoding a 1-deoxy-D-xylulose 5-phosphate reductoisomerase polypeptide having at least 93% identity, based on the Clustal V method of alignment, when compared to one of SEQ ID NO:6, 8, 16, 18, 20 or 24.

This invention also includes the isolated complement of such polynucleotides, wherein the complement and the polynucleotide consist of the same number of nucleotides, and the nucleotide sequences of the complement and the polynucleotide have 100% complementarity.

Nucleic acid fragments encoding at least a portion of 1-deoxy-D-xylulose 5-phosphate reductoisomerase have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other 1-deoxy-D-xylulose 5-phosphate reductoisomerases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, and 23, and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as 1-deoxy-D-xylulose 5-phosphate reductoisomerases) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, and 23, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of plastid IPP in those cells. Because this mevalonate-independent pathway appears to be unique to microorganisms and plant plastids inhibitors of 1-deoxy-D-xylulose 5-phosphate reductoisomerases should have no affect on animals making this enzyme an excellent herbicide candidate. Overexpression of the 1-deoxy-D-xylulose 5-phosphate reductoisomerase gene will produce the active enzyme for high-throughput screening to find inhibitors for this enzyme. These inhibitors may lead to the discovery of novel herbicides.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptide to different cellular compartments, or to facilitate its secretion from the cell. It is thus envisioned that the chimeric gene described above may be further supplemented by altering the coding sequence to encode the instant polypeptide with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded 1-deoxy-D-xylulose 5-phosphate reductoisomerase. An example of a vector for high level expression of the instant polypeptides in a bacterial host is provided (Example 6).

Additionally, the instant polypeptides can be used as a targets to facilitate design and/or identification of inhibitors of those enzymes that may be useful as herbicides. This is desirable because the polypeptide described herein catalyzes isopentenyl diphosphate synthesis via the mevalonate-independent pathway. Accordingly, inhibition of the activity of the enzyme described herein could lead to inhibition of plant growth. Accordingly, inhibition of the activity of 1-deoxy-D-xylulose 5-phosphate reductoisomerase could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al. (1995) *Proc. Natl. Acad. Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---|---|---|
| cen3n | Corn Endosperm 20 Days After Pollination* | cen3n.pk0157.e12 |
| cho1c | Corn Embryo 20 Days After Pollination | cho1c.pk004.f12 |
| cr1n | Corn Root From 7 Day Old Seedlings* | cr1n.pk0095.g3 |
| csi1 | Corn Silk | csi1.pk0041.f11 |
| p0004 | Corn Immature Ear | p0004.cb1hh74r |
| p0006 | Corn Young Shoot | p0006.cbyvo28r |
| p0012 | Corn Middle 3/4 of the 3rd Leaf Blade and Mid Rib From Green Leaves Treated with Jasmonic Acid (1 mg/ml in 0.02% Tween 20) for 24 Hours Before Collection | p0012.cglac07r |
| rlr6 | Rice Leaf 15 Days After Germination, 6 Hours After Infection of Strain *Magaporthe grisea* 4360-R-62 (AVR2-YAMO); Resistant | rlr6.pk0073.d5 |
| ses2w | Soybean Embryogenic Suspension Two Weeks After Subculture | ses2w.pk0029.e5 |

TABLE 2-continued cDNA Libraries from Corn, Rice, Soybean, and Wheat

| Library | Tissue | Clone |
|---|---|---|
| sgc3c | Soybean Cotyledon 14-21 Days After Germination (Starting to Turn Yellow) | sgc3c.pk001.d16 |
| sl1 | Soybean Two-Week-Old Developing Seedlings | sl1.pk0021.a6 |
| sl1 | Soybean Two-Week-Old Developing Seedlings | sl1.pk0036.a5 |
| sl1 | Soybean Two-Week-Old Developing Seedlings | sl1.pk152.i19 |
| sl2 | Soybean Two-Week-Old Developing Seedlings Treated With 2.5 ppm chlorimuron | sl2.pk0039.d4 |
| sl2 | Soybean Two-Week-Old Developing Seedlings Treated With 2.5 ppm chlorimuron | sl2.pk0111.c9 |
| sl2 | Soybean Two-Week-Old Developing Seedlings Treated With 2.5 ppm chlorimuron | sl2.pk124.p17 |
| sl2 | Soybean Two-Week-Old Developing Seedlings Treated With 2.5 ppm chlorimuron | sl2.pk125.m18 |
| sml1c | Soybean Mature Leaf | sml1c.pk001.c15 |
| sml1c | Soybean Mature Leaf | sml1c.pk005.a24 |
| sr1 | Soybean Root | sr1.pk0008.d1 |
| srm | Soybean Root Meristem | srm.pk0014.f8 |
| wlm12 | Wheat Seedlings 12 Hours After Inoculation With *Erysiphe graminis* f. sp *tritici* | wlm12.pk0003.d11 |
| wlm24 | Wheat Seedlings 24 Hours After Inoculation With *Erysiphe graminis* f. sp *tritici* | wlm24.pk0014.d7 |
| wr1 | Wheat Root From 7 Day Old Seedling | wr1.pk0084.a4 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Example 2

Identification of cDNA Clones cDNA clones encoding 1-deoxy-D-xylulose5-phosphate reductoisomerases were identified by conducting BLAST (Basic Local Alignment Search Tool; Altschul et al. (1993) J. Mol. Biol. 215:403-410) searches for similarity to sequences contained in the BLAST "nr" database (comprising all non-redundant Gen Bank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) Nat. Genet. 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding 1-Deoxy-D-Xylulose 5-Phosphate Reductoisomerase The BLASTX search using the EST sequences from clones listed in Table 3 revealed similarity of the polypeptides encoded by the cDNAs to 1-deoxy-D-xylulose 5-phosphate reductoisomerase from *Synechocystis* PCC6803 and *Escherichia coli* (NCBI General Identifier Nos. 1001556 and 3434984, respectively). Shown in Table 3 are the BLAST results for individual ESTs ("EST"), contigs assembled from two or more ESTs ("Contig"), or sequences encoding the entire protein derived from the entire cDNA inserts comprising the indicated cDNA clones ("FIS"), a contig, or an FIS and PCR ("CGS"):

TABLE 3

BLAST Results for Sequences Encoding Polypeptides Homologous to 1-Deoxy-D-Xylulose 5-Phosphate Reductoisomerase

|  |  | BLAST pLog Score | |
|---|---|---|---|
| Clone | Status | 1001556 | 3434984 |
| Contig of:<br>p0004.cb1hh74r<br>p0012.cglac07r<br>p0006.cbyvo28r | Contig | 14.40 | 10.70 |
| Contig of:<br>cen3n.pk0157.e12<br>cr1n.pk0095.g3<br>cho1c.pk004.f12<br>csi1.pk0041.f11 | Contig | 111.0 | 59.52 |
| rlr6.pk0073.d5 | CGS | 164.0 | 94.0 |
| Contig of:<br>sml1c.pk001.c15<br>sml1c.pk005.a24<br>sl1.pk0021.a6<br>sl2.pk124.p17<br>sl1.pk0036.a5<br>sl2.pk0111.c9<br>sl1.pk152.i19<br>sl2.pk0039.d4 | CGS | 154.0 | 85.50 |
| Contig of:<br>sr1.pk0008.d1<br>sr1.pk0007.c11<br>srm.pk0014.f8 | Contig | 64.40 | 32.40 |
| Contig of:<br>wlm12.pk0003.d11<br>wr1.pk0084.a4 | Contig | 12.70 | 9.30 |
| wlm24.pk0014.d7 | EST | 24.70 | 10.70 |

Further sequencing of some of the above clones yielded new information. The BLASTX search using the nucleotide sequences from clones listed in Table 4 revealed similarity of the polypeptides encoded by the cDNAs to 1-deoxy-D-xylulose 5-phosphate reductoisomerase from *Arabidopsis thaliana*, *Mentha×piperita*, and *Synechocystis* sp. (NCBI General Identifier Nos. 4886307, 4581856, and 2496789, respectively).

The 1-deoxy-D-xylulose 5-phosphate reductoisomerase from *Arabidopsis thaliana* (NCBI General Identifier No. 4886307; SEQ ID NO:21), is a 406 amino acid fragment that has been cloned in *E. coli* and shown to have enzymatic activity (Schwender et al. (1999) *FEBS Lett* 455:140-144).

Shown in Table 4 are the BLAST results for the sequences of the entire cDNA inserts comprising the indicated cDNA clones ("FIS"), contigs assembled from an FIS and an EST ("Contig*"), or sequences encoding the entire protein derived from an FIS, or an FIS and PCR ("CGS"):

TABLE 4

BLAST Results for Sequences Encoding Polypeptides Homologous to 1-Deoxy-D-Xylulose 5-Phosphate Reductoisomerase

|  |  | BLAST pLog Score | | |
|---|---|---|---|---|
| Clone | Status | 4886307 | 4581856 | 2496789 |
| p0004.cb1hh74r | CGS | >254.00 | >254.00 | >254.00 |
| Contig of:<br>ses2w.pk0029.e5<br>sgc3c.pk001.d16<br>sr1.pk0008.d1:fis | CGS | >254.00 | >254.00 | >254.00 |
| wlm12.pk0003.d11:fis | FIS | 145.00 | 145.00 | 145.00 |

Another soybean clone, sl2.pk125.m18, was identified that corresponds to the gene of SEQ ID NOs:7 and 8. Full-insert sequencing of the soybean clone sl2.pk125.m18 was performed and is present as SEQ ID NO:23. The corresponding amino acid sequence is present as SEQ ID NO:24. The FIS sequence of sl2.pk125.m18 was used to identify sequencing errors in the contig sequence of SEQ ID NO:7 (contig containing sml1c.pk001.c15), and the corresponding amino acid sequence of SEQ ID NO:8. For SEQ ID NO:8, the amino acid residues at position 325 and 330 should have been glutamine (Q) and isoleucine (I), respectively, and there is a frame-shift occurring after amino acid 461.

NCBI General Identifier No. 4581856 (SEQ ID NO:22), the amino acid sequence of 1-deoxy-D-xylulose 5-phosphate reductoisomerase from *Mentha×piperita*, was replaced on Oct. 7, 2005, by NCBI General Identifier No. 77378042 (SEQ ID NO:25).

FIGS. 1A-1C present an alignment of the amino acid sequences set forth in SEQ ID NOs:6, 16, 18, 20, and 24 and the *Arabidopsis thaliana* and *Mentha x piperita* sequences (SEQ ID NO:21 and SEQ ID NO:25). The data in Table 5 represents a calculation of the percent identity of the amino acid sequences set forth in SEQ ID NOs:6, 16, 18, 20, and 24 and the *Arabidopsis thaliana* and *Mentha x piperita* sequences (SEQ ID NO:21 and SEQ ID NO:25).

TABLE 5

Percent Identity of Amino Acid Sequences Deduced From the Nucleotide Sequences of cDNA Clones Encoding Polypeptides Homologous to 1-Deoxy-D-Xylulose 5-Phosphate Reductoisomerase

|  |  | Percent Identity to SEQ ID NO: | |
|---|---|---|---|
| SEQ ID NO. | Plant | 21 (GI No. 4886307) | 25 (GI No. 77378042) |
| 6 | Rice | 91.6 | 79.1 |
| 16 | Corn | 90.9 | 79.6 |
| 18 | Soybean | 88.4 | 79.6 |
| 20 | Wheat | 89.7 | 78.1 |
| 24 | Soybean | 78.1 | 71.8 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5. Sequence alignments and BLAST scores and probabilities indicate that the nucleic acid fragments comprising the instant cDNA clones encode one corn, one rice, one wheat, and two soybean 1-deoxy-D-xylulose 5-phosphate reductoisomerase. These sequences represent the first corn, rice, soybean, and wheat sequences encoding 1-deoxy-D-xylulose 5-phosphate reductoisomerase.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue; Stratagene). Bacterial transformants can be screened by restriction enzyme digestion of plasmid DNA and limited nucleotide sequence analysis using the dideoxy chain termination method (Sequenase DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™low melting agarose gel (FMC). Buffer and agarose contain 10 µg/ml ethidium bromide for visualization of the DNA fragment. The fragment can then be purified from the agarose gel by digestion with GELase™(Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 7

Evaluating Compounds for Their Ability to Inhibit the Activity of 1-Deoxy-D-Xylulose 5-Phosphate Reductoisomerase The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$" or "His-tag"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for 1-deoxy-D-xylulose 5-phosphate reductoisomerase are presented by Kuzuyama et al. (1998) *Tetrahedron lett.* 39:4509-4512, Schwender et al. (1999) *FEBS Lett* 455:140-144, and Lange et al. (1999) *Arch Biochem Biophys* 365:170-174.

Example 8

Expression of His-Tagged 1-Deoxy-D-Xylulose 5-Phosphate Reductoisomerase Proteins in *E. coli*

The 1-deoxy-D-xylulose 5-phosphate reductoisomerase (DXR) polypeptides from *E. coli*, *Synechocystis*, and rice were cloned and expressed in *E. coli* as histidine-tagged (His-tagged) proteins. Each His-tagged DXR polypeptide has a twenty amino acid N-terminal extension (SEQ ID NO:26) that contains six consecutive histidine residues. *E. coli* expression vectors were constructed containing polynucleotides encoding the following His tagged DXR polypeptides: *E. coli* His-DXR (SEQ ID NO:27); *Synechocystis* His-DXR (SEQ ID NO:28); full-length rice His-DXR (SEQ ID NO:29); and a truncated rice His-DXR (SEQ ID NO:30), in which most of the putative chloroplast transit peptide (i.e., the N-terminal 51 amino acid fragment), has been removed.

Recombinant His-tagged DXR proteins were purified from *E. coli* using Ni-Agarose. Recombinant DXR activity was measured using a non-radioactive kinetic assay (Kuzuyama et al. (1998) *Tetrahedron Lett* 39:7913-7916). The assay mixture contained the following: 100 mM Hepes (pH 7.5); 1 mM $MnCl_2$; 0.3 nM NADPH, DXR, and 0.3 mM 1-deoxy-D-xylulose 4-phosphate (DXP). The final volume of the reaction mixture was 200 μl and the assay was initiated by adding the substrate. The assay was run at room temperature on a plate reader. The oxidation of NADPH was monitored at 340 nm. The DXR activity was determined from the slope of the kinetic curve.

DXR activity was detected for the *E. coli* His-DXR (SEQ ID NO:27) and the *Synechocystis* His-DXR (SEQ ID NO:28). Expression of the full-length rice His-DXR (SEQ ID NO:29) in *E. coli* did not produce soluble protein in the Ni-Agarose purified fraction. The full-length rice His-DXR protein (SEQ ID NO:29) contains the chloroplast transit peptide for the rice DXR protein. A truncated rice His-DXR (SEQ ID NO:30), when expressed in *E. coli*, produced a soluble 46-kD protein in the Ni-Agarose purified fraction; however, no oxidation of NADPH was detected. The polypeptide of SEQ ID NO:30 consists of a rice DXR protein in which the first fifty-one amino acids have been removed and replaced with a twenty amino acid His-tag. A second truncated rice His-DXR polypeptide (SEQ ID NO:31) was also expressed in *E. coli*. SEQ ID NO:31 consists of a rice DXR protein in which the first seventy-six amino acids have been removed and replaced with a twenty-one amino acid His-tag. A soluble protein was visible in the Ni-Agarose purified fraction from *E. coli* expressing the second truncated rice His-DXR (SEQ ID NO:31); however, no oxidation of NADPH was detected.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide comprising:
   (a) a nucleotide sequence encoding a polypeptide having 1-deoxy-D-xylulose 5-phosphate reductoisomerase activity, wherein the polypeptide has an amino acid sequence of at least 93% sequence identity, based on the Clustal V method of alignment, when compared to SEQ ID NO: 18, or
   (b) a complement of the nucleotide sequence, wherein the complement and the nucleotide sequence consist of the same number of nucleotides and are 100% complementary.
2. The polynucleotide of claim 1, wherein the amino acid sequence of the polypeptide has at least 95% sequence identity, based on the Clustal V method of alignment, when compared to SEQ ID NO:18.
3. The polynucleotide of claim 1, wherein the amino acid sequence of the polypeptide has at least 98% sequence identity, based on the Clustal V method of alignment, when compared to SEQ ID NO:18.
4. The polynucleotide of claim 1, wherein the amino acid sequence of the polypeptide comprises SEQ ID NO:18.
5. The polynucleotide of claim 1 wherein the nucleotide sequence comprises SEQ ID NO:17.
6. A vector comprising the polynucleotide of claim 1.
7. A recombinant DNA construct comprising the polynucleotide of claim 1 operably linked to at least one regulatory sequence.
8. A method for transforming a cell, comprising transforming a cell with the polynucleotide of claim 1.
9. A cell comprising the recombinant DNA construct of claim 7, wherein the cell is selected from the group consisting of: a yeast cell, a bacterial cell and a plant cell.
10. A method for producing a transgenic plant comprising transforming a plant cell with the polynucleotide of claim 1 and regenerating a transgenic plant from the transformed plant cell.
11. A plant comprising the recombinant DNA construct of claim 7.
12. A seed comprising the recombinant DNA construct of claim 7.
13. A method for isolating a polypeptide having 1-deoxy-D-xylulose 5-phosphate reductoisomerase activity comprising isolating the polypeptide from a cell or culture medium of the cell, wherein the cell comprises a recombinant DNA construct comprising the polynucleotide of claim 1 operably linked to at least one regulatory sequence.

14. A method of altering the level of expression of a 1-deoxy-D-xylulose 5-phosphate reductoisomerase in a host cell comprising: (a) transforming a host cell with the recombinant DNA construct of claim 7; and (b) growing the transformed host cell under conditions that are suitable for expression of the recombinant DNA construct wherein expression of the recombinant DNA construct results in production of altered levels of the 1-deoxy-D-xylulose 5-phosphate reductoisomerase in the transformed host cell.

15. A method for evaluating at least one compound for its ability to inhibit 1-deoxy-D-xylulose 5-phosphate reductoisomerase activity, comprising the steps of:
  (a) introducing into a host cell the recombinant DNA construct of claim 7;
  (b) growing the host cell under conditions that are suitable for expression of the recombinant DNA construct wherein expression of the recombinant DNA construct results in production of a 1-deoxy-D-xylulose 5-phosphate reductoisomerase;
  (c) optionally purifying the 1-deoxy-D-xylulose 5-phosphate reductoisomerase expressed by the recombinant DNA construct in the host cell;
  (d) treating the 1-deoxy-D-xylulose 5-phosphate reductoisomerase with a test compound;
  (e) comparing the activity of the 1-deoxy-D-xylulose 5-phosphate reductoisomerase that has been treated with the test compound to the activity of an untreated 1-deoxy-D-xylulose 5-phosphate reductoisomerase, and (f) selecting the test compound if it has an inhibitory effect on the activity of 1-deoxy-D-xylulose 5-phosphate reductoisomerase based on said comparison of said step (e).

* * * * *

SEQUENCE LISTING

<160> NUMBER OF SEQ ID NOS: 31

<210> SEQ ID NO 1
<211> LENGTH: 565
<212> TYPE: DNA

```
<213> ORGANISM: Zea mays
<220> FEATURE:
<221> NAME/KEY: unsure
<222> LOCATION: (5)..(9)
<223> OTHER INFORMATION: n = A, C, G, or T
<220> FEATURE:
<221> NAME/KEY: unsure
<222> LOCATION: (450)
<223> OTHER INFORMATION: n = A, C, G, or T
<220> FEATURE:
<221> NAME/KEY: unsure
<222> LOCATION: (549)
<223> OTHER INFORMATION: n = A, C, G, or T

<400> SEQUENCE: 1
aatgnnnnna tcaggctgtt acataggggg gcttgcattg tacacaccca acctggccta      60
gcctacccta ctacactcgt gccgattcgg cacgagcagc gacggtcgcc accaccgctc     120
ccctccctct cccctcctc gcccagcggc aattaccaca gcctcccag caagccggga      180 tggctgcact caaggcatcg ttccggggtg agctcagcgc cgcttccttc ctcgactcca     240 gcagggacc tctcgtccag cacaaagtgg attttacgtt tcaaaggaag ggcaaacgag     300
ctatttcact gagaaggaca tgctgttcta tgcaacaggc tccaccacca gcatggcctg     360
ggcgagctgt tgctgagcct ggccggagtc atgggatggc ccaaagccta tctcgattgt     420
tggttcaact ggttccatag gaacacagan attggacatt gttgcggaga atcctgataa     480
gttcagagtt gttgctcttg ctgctggatc caatgtcacg cttctagctg atcaggtcaa     540
aacattcana cctaagttgg ttcgg                                           565

<210> SEQ ID NO 2
<211> LENGTH: 63
<212> TYPE: PRT
<213> ORGANISM: Zea mays
<220> FEATURE:
<221> NAME/KEY: UNSURE
<222> LOCATION: (25)
<223> OTHER INFORMATION: Xaa = ANY AMINO ACID
<220> FEATURE:
<221> NAME/KEY: UNSURE
<222> LOCATION: (58)
<223> OTHER INFORMATION: Xaa = ANY AMINO ACID

<400> SEQUENCE: 2

Ala Trp Pro Glu Ser Trp Asp Gly Pro Lys Pro Ile Ser Ile Val Gly
 1               5                  10                  15

Ser Thr Gly Ser Ile Gly Thr Gln Xaa Leu Asp Ile Val Ala Glu Asn
            20                  25                  30

Pro Asp Lys Phe Arg Val Val Ala Leu Ala Ala Gly Ser Asn Val Thr
        35                  40                  45

Leu Leu Ala Asp Gln Val Lys Thr Phe Xaa Pro Lys Leu Val Arg
    50                  55                  60

<210> SEQ ID NO 3
<211> LENGTH: 868
<212> TYPE: DNA
<213> ORGANISM: Zea mays
<220> FEATURE:
<221> NAME/KEY: unsure
<222> LOCATION: (343)
<223> OTHER INFORMATION: n = A, C, G, or T
<220> FEATURE:
<221> NAME/KEY: unsure
<222> LOCATION: (356)
<223> OTHER INFORMATION: n = A, C, G, or T
<220> FEATURE:
<221> NAME/KEY: unsure
<222> LOCATION: (367)
```

<223> OTHER INFORMATION: n = A, C, G, or T
<220> FEATURE:
<221> NAME/KEY: unsure
<222> LOCATION: (789)
<223> OTHER INFORMATION: n = A, C, G, or T
<220> FEATURE:
<221> NAME/KEY: unsure
<222> LOCATION: (862)
<223> OTHER INFORMATION: n = A, C, G, or T

<400> SEQUENCE: 3

```
gatgaattga agaagccttt ggctgattgc gaagagaagc cagaaattat tcctggggag      60
caaggtgtca tagaagttgc tcgccatcca gatgcagtta cagttgtcac agggatagta     120
ggttgtgcag ggctgaagcc tacagttgct gcaattgaag ctggtaaaga catagcattg     180
gcaaacaaag agacacttat tgcaggtggt cctttttgtgc ttccccttgc acacaaacac    240
aaagtgaaaa ttcttccagc tgattctgag cactctgcaa tatttcagtg tatacaaggc    300
ttgtccgaag gtgcacttcg tcgcattatt ctaactgcat cangtggtgc tttcanggac    360
tggccanttg acaggctgaa agatgtaaaa gttgctgacg ctttaaagca tccaaactgg    420
aatatgggaa ggaagatcac agtagattct gctactttat tcaacaaggg tttagaagtt    480
attgaagcac attatttatt tggtgctgaa tatgatgaca ttgagattgt gattcaccca    540
cagtctatca tacactctat ggttgaaacc caggattcat ctgtcctagc tcagttggga    600
tggccagata tgcggttacc aatcttatac accttatcat ggccagatag gagtcctgag    660
cgctgctaat gagaaggccg tggagttgtt cattgacgag aagattagct acctggacat    720
attcaaggtg gtggagctta catgtaacgc gcatcggaac agctggtaac aaccgtcact    780
ggaggaatng tcattacatc gtggcaagaa tatgcagcat cacaacatct ctggctgagc    840
tgtcctgcat atagtctcac anacttgt                                        868
```

<210> SEQ ID NO 4
<211> LENGTH: 217
<212> TYPE: PRT
<213> ORGANISM: Zea mays
<220> FEATURE:
<221> NAME/KEY: UNSURE
<222> LOCATION: (115)
<223> OTHER INFORMATION: Xaa = ANY AMINO ACID
<220> FEATURE:
<221> NAME/KEY: UNSURE
<222> LOCATION: (119)
<223> OTHER INFORMATION: Xaa = ANY AMINO ACID
<220> FEATURE:
<221> NAME/KEY: UNSURE
<222> LOCATION: (123)
<223> OTHER INFORMATION: Xaa = ANY AMINO ACID

<400> SEQUENCE: 4

```
Asp Glu Leu Lys Glu Ala Leu Ala Asp Cys Glu Glu Lys Pro Glu Ile
 1               5                  10                  15

Ile Pro Gly Glu Gln Gly Val Ile Glu Val Ala Arg His Pro Asp Ala
                20                  25                  30

Val Thr Val Val Thr Gly Ile Val Gly Cys Ala Gly Leu Lys Pro Thr
            35                  40                  45

Val Ala Ala Ile Glu Ala Gly Lys Asp Ile Ala Leu Ala Asn Lys Glu
        50                  55                  60

Thr Leu Ile Ala Gly Gly Pro Phe Val Leu Pro Leu Ala His Lys His
65                  70                  75                  80

Lys Val Lys Ile Leu Pro Ala Asp Ser Glu His Ser Ala Ile Phe Gln
                85                  90                  95
```

```
Cys Ile Gln Gly Leu Ser Glu Gly Ala Leu Arg Arg Ile Ile Leu Thr
                100                 105                 110

Ala Ser Xaa Gly Ala Phe Xaa Asp Trp Pro Xaa Asp Arg Leu Lys Asp
            115                 120                 125

Val Lys Val Ala Asp Ala Leu Lys His Pro Asn Trp Asn Met Gly Arg
130                 135                 140

Lys Ile Thr Val Asp Ser Ala Thr Leu Phe Asn Lys Gly Leu Glu Val
145                 150                 155                 160

Ile Glu Ala His Tyr Leu Phe Gly Ala Glu Tyr Asp Asp Ile Glu Ile
                165                 170                 175

Val Ile His Pro Gln Ser Ile Ile His Ser Met Val Glu Thr Gln Asp
            180                 185                 190

Ser Ser Val Leu Ala Gln Leu Gly Trp Pro Asp Met Arg Leu Pro Ile
            195                 200                 205

Leu Tyr Thr Leu Ser Trp Pro Asp Arg
    210                 215

<210> SEQ ID NO 5
<211> LENGTH: 1901
<212> TYPE: DNA
<213> ORGANISM: Oryza sativa

<400> SEQUENCE: 5
acactatgac catgattacg ccaagcgcgc aattaaccct cactaaaggg aacaaaagct      60
ggagctccac cgcggtggcg gccgctctag aactagtgga tccccggggc tgcaggaatt     120
cggcacgagg tttaaaccag acgtcgagtc gagcattaac tcagtcaggg tggccatggc     180
gctcaaggtc gtctctttcc ccggggactt ggccgcggtc tcattcctcg actccaacag     240
aggaggagct ttcaaccagc tcaaagtgga cctcccgttt caaacgaggg acagaagagc     300
agtttccctg agaaggactt gctgttcaat gcaacaggct ccaccaccag catggcctgg     360
tcgagccgtt gttgaacctg ggaggaggtc atgggatggc cccaagccta tctcaattgt     420
tggctcaacc ggttctattg cacacagac attggacata gttgcggaga atccagataa     480
attccgggtt gttgctcttg ctgctggctc caatgtgact cttctagctg atcaggtgaa     540 acattcaaa ccaaagcttg ttgctgtaag aaatgagtca ttagttgatg agctaaagga     600
agccttagct gattgtgatt ggaagccaga aattattcct ggtgagcaag gtgtcataga     660
ggttgctcgc cacccagatg cagttacagt tgttactggg atagtagggt gtgcaggact     720
gaagcctaca gttgctgcaa ttgaagctgg gaaagatata gcattggcga acaaagagac     780
acttattgca ggtggtcctt ttgtgcttcc ccttgcacaa aagcacaaag tgaaaatact     840
tcctgctgat tctgagcact ctgctatatt tcagtgtata caaggcttgc ccgaaggagc     900
acttcgccgc attattttga ctgcatcagg tggtgctttc agggactggc cagttgacaa     960
gttgaaagaa gtaaaagttg ctgatgcttt aaagcacccg aactggaata tggggaagaa    1020
gattactgta gattctgcta cattattcaa caagggttta gaagttattg aagcacatta    1080
tttatttggt gctgaatacg atgacattga aattgtgatc cacccacaat ctatcataca    1140
ctctatgatt gaaacccagg attcatctgt gttggctcaa ctgggatggc cagatatgcg    1200
gataccaacc ttatacacca tgtcttggcc agacagaatc tattgctcag aggtcacctg    1260
gccccgacta gatctttgca agctgggttc actgacattc aaagctcctg acaatgtgaa    1320
atacccgtcg atggatctcg cctatgcagc tggaagagct ggggggcacca tgacaggagt    1380 tctgagtgct gctaatgaga aggctgtgga gttgttcatc gatgaaaaga tcgggtacct    1440
```

-continued

```
ggacatcttc aaggtggtgg agctgacatg cgacgctcat cggaatgagc tagtaacaag    1500
gccatcactg gaggagatca tacattatga tctgtgggcg agggagtatg ctgccagcct    1560
acagccatcc actggcctca gccctgtacc tgtctagtac ttgtagcaat acaaaattac    1620
agtagcattg tacactactg ccgtgccagc tccatgcata gtcagcagct ggccactctc    1680
tagctatatc tagatgcgag agaattttaa ggatgtaaat catgccttca catgaataaa    1740
tcgttcgtcc gtgcgttgtg tattcatgta aattttgacg gatggtcaag taaaaataac    1800
aatggcaaat taatttaggg aaaaaaaaaa aaaaaaaact cgaggggggg cccggtaccc    1860
aattcgccct atagtgagtc gtattacgcg cgctcactgg c                         1901
```

<210> SEQ ID NO 6
<211> LENGTH: 473
<212> TYPE: PRT
<213> ORGANISM: Oryza sativa

<400> SEQUENCE: 6

```
Met Ala Leu Lys Val Val Ser Phe Pro Gly Asp Leu Ala Ala Val Ser
  1               5                  10                  15

Phe Leu Asp Ser Asn Arg Gly Gly Ala Phe Asn Gln Leu Lys Val Asp
             20                  25                  30

Leu Pro Phe Gln Thr Arg Asp Arg Ala Val Ser Leu Arg Arg Thr
         35                  40                  45

Cys Cys Ser Met Gln Gln Ala Pro Pro Ala Trp Pro Gly Arg Ala
     50                  55                  60

Val Val Glu Pro Gly Arg Arg Ser Trp Asp Gly Pro Lys Pro Ile Ser
 65                  70                  75                  80

Ile Val Gly Ser Thr Gly Ser Ile Gly Thr Gln Thr Leu Asp Ile Val
                 85                  90                  95

Ala Glu Asn Pro Asp Lys Phe Arg Val Val Ala Leu Ala Ala Gly Ser
            100                 105                 110

Asn Val Thr Leu Leu Ala Asp Gln Val Lys Thr Phe Lys Pro Lys Leu
        115                 120                 125

Val Ala Val Arg Asn Glu Ser Leu Val Asp Glu Leu Lys Glu Ala Leu
    130                 135                 140

Ala Asp Cys Asp Trp Lys Pro Glu Ile Ile Pro Gly Glu Gln Gly Val
145                 150                 155                 160

Ile Glu Val Ala Arg His Pro Asp Ala Val Thr Val Thr Gly Ile
                165                 170                 175

Val Gly Cys Ala Gly Leu Lys Pro Thr Val Ala Ala Ile Glu Ala Gly
            180                 185                 190

Lys Asp Ile Ala Leu Ala Asn Lys Glu Thr Leu Ile Ala Gly Gly Pro
        195                 200                 205

Phe Val Leu Pro Leu Ala Gln Lys His Lys Val Lys Ile Leu Pro Ala
    210                 215                 220

Asp Ser Glu His Ser Ala Ile Phe Gln Cys Ile Gln Gly Leu Pro Glu
225                 230                 235                 240

Gly Ala Leu Arg Arg Ile Ile Leu Thr Ala Ser Gly Gly Ala Phe Arg
                245                 250                 255

Asp Trp Pro Val Asp Lys Leu Lys Glu Val Lys Val Ala Asp Ala Leu
            260                 265                 270

Lys His Pro Asn Trp Asn Met Gly Lys Lys Ile Thr Val Asp Ser Ala
        275                 280                 285

Thr Leu Phe Asn Lys Gly Leu Glu Val Ile Glu Ala His Tyr Leu Phe
    290                 295                 300
```

```
Gly Ala Glu Tyr Asp Asp Ile Glu Ile Val Ile His Pro Gln Ser Ile
305                 310                 315                 320

Ile His Ser Met Ile Glu Thr Gln Asp Ser Ser Val Leu Ala Gln Leu
            325                 330                 335

Gly Trp Pro Asp Met Arg Ile Pro Thr Leu Tyr Thr Met Ser Trp Pro
            340                 345                 350

Asp Arg Ile Tyr Cys Ser Glu Val Thr Trp Pro Arg Leu Asp Leu Cys
            355                 360                 365

Lys Leu Gly Ser Leu Thr Phe Lys Ala Pro Asp Asn Val Lys Tyr Pro
        370                 375                 380

Ser Met Asp Leu Ala Tyr Ala Ala Gly Arg Ala Gly Gly Thr Met Thr
385                 390                 395                 400

Gly Val Leu Ser Ala Ala Asn Glu Lys Ala Val Glu Leu Phe Ile Asp
                405                 410                 415

Glu Lys Ile Gly Tyr Leu Asp Ile Phe Lys Val Val Glu Leu Thr Cys
                420                 425                 430

Asp Ala His Arg Asn Glu Leu Val Thr Arg Pro Ser Leu Glu Glu Ile
            435                 440                 445

Ile His Tyr Asp Leu Trp Ala Arg Glu Tyr Ala Ala Ser Leu Gln Pro
    450                 455                 460

Ser Thr Gly Leu Ser Pro Val Pro Val
465                 470

<210> SEQ ID NO 7
<211> LENGTH: 1592
<212> TYPE: DNA
<213> ORGANISM: Glycine max
<220> FEATURE:
<221> NAME/KEY: unsure
<222> LOCATION: (993)
<223> OTHER INFORMATION: n = A, C, G, or T
<220> FEATURE:
<221> NAME/KEY: unsure
<222> LOCATION: (1402)
<223> OTHER INFORMATION: n = A, C, G, or T

<400> SEQUENCE: 7
gctggttcaa ctgaggtgat ggctttgaat ttgccttctc ccgcccaagt gaagcccttg     60 ttttctctt caaataactc cacaaaactt ccaggtagct tttctttgaa gagaaaagat    120
agtgacacaa cagtagagag acgagtttat tgctctgccg ctgctcaatc accaccacca    180
gcatggccag aacagctat tcccgagcct tctgatttca agacatggga tgggcaaaaa    240
cctatttctg tcttaggatc tacgggttca attggaactc agacactgag tatagtggct    300
gagttcccaa aaagatttaa agttgtgagc cttgctgctg ctctaatat tactcttctt    360 gctgaccaga ttaaaacatt taagcctgaa gttgttggtc ttagaaatga gtctttaatt    420
gatgaactca agaggctttt ggctgatgtg atcacaaaac ccgaaatcat ccctggagag    480
caaggagtca ttgaggccgc tcgtcaccct gatgccacca ctgtagttac aggcatagtt    540
ggttgtgcag gattaaagcc aacagttgca gcaattgaag cagggaaaga catagcattg    600
gccaacaaag agacaatgat tgcgggagcc ccttttgttc ttcctcttgc tcacaaacat    660
aacataaaaa ttcttcccgc tgattcggaa cattctgcaa ttttttcagtc tatccagggg    720 ttgccaaagg gtgcacttag gaaaatcctt ttaactggat caggaggtgc tttcagagaa    780
tggcctgctg aaaagatgaa agatattaag cttgctgatg cattaaagca tcccatatgg    840
agtttgggga gaaaaataac tattgactct gctaccccttt tcaataaggg tctagaagta    900
```

-continued

```
attgaagcac attacttgtt tggagcaagc tatgacgata ttgagattgt tattcatcct    960
caatccatca tacattcctt ggttgaaacg cangattcat ctgttaatgc acagttgggg   1020
atacctgaca tgcgcttacc gctcctttat acattatctt ggccagaaag aatctattgc   1080
tctgaagtaa cttggcctcg tcttgatctt agcaagtatg ttctctaac attttatgca    1140 ccggatgaca agaagtttcc atcggtgaat ctttgctatg ctgcgggacg tgctggaggc   1200
accatgacag gagttcttag tgcagcaaat gagaaagctg tagaaatgtt tgttgaagaa   1260
aagattagtt atctggatat attcaaggtt gtggaactaa cttgtcagga acatcaaaag   1320
gaattagtag catctccgtc actcgaagaa attattcact atgaccaatg ggctcgacaa   1380
tatgctgcta gtctgcaaaa angcttcaag tgtttgaatc ccatatttct gacatatttt   1440
agaagttggg gctgtggtgg attgttggca actgctagca tattttgtaa atgtattgtt   1500
ggttcatcaa tcttgtaaaa tgtaaagggg taagctatat aaagtatatg tactcctaaa   1560
agggtttcaa taaaagttct agcttcaaga aa                                 1592
```

<210> SEQ ID NO 8
<211> LENGTH: 499
<212> TYPE: PRT
<213> ORGANISM: Glycine max
<220> FEATURE:
<221> NAME/KEY: UNSURE
<222> LOCATION: (325)
<223> OTHER INFORMATION: Xaa = ANY AMINO ACID
<220> FEATURE:
<221> NAME/KEY: UNSURE
<222> LOCATION: (462)
<223> OTHER INFORMATION: Xaa = ANY AMINO ACID

<400> SEQUENCE: 8

```
Met Ala Leu Asn Leu Pro Ser Pro Ala Gln Val Lys Pro Leu Phe Phe
  1               5                  10                  15

Ser Ser Asn Asn Ser Thr Lys Leu Pro Gly Ser Phe Ser Leu Lys Arg
             20                  25                  30

Lys Asp Ser Asp Thr Thr Val Glu Arg Arg Val Tyr Cys Ser Ala Ala
         35                  40                  45

Ala Gln Ser Pro Pro Ala Trp Pro Gly Thr Ala Ile Pro Glu Pro
     50                  55                  60

Ser Asp Phe Lys Thr Trp Asp Gly Gln Lys Pro Ile Ser Val Leu Gly
 65                  70                  75                  80

Ser Thr Gly Ser Ile Gly Thr Gln Thr Leu Ser Ile Val Ala Glu Phe
                 85                  90                  95

Pro Glu Arg Phe Lys Val Val Ser Leu Ala Ala Gly Ser Asn Ile Thr
            100                 105                 110

Leu Leu Ala Asp Gln Ile Lys Thr Phe Lys Pro Glu Val Val Gly Leu
        115                 120                 125

Arg Asn Glu Ser Leu Ile Asp Glu Leu Lys Glu Ala Leu Ala Asp Val
    130                 135                 140

Asp His Lys Pro Glu Ile Ile Pro Gly Glu Gln Gly Val Ile Glu Ala
145                 150                 155                 160

Ala Arg His Pro Asp Ala Thr Thr Val Val Thr Gly Ile Val Gly Cys
                165                 170                 175

Ala Gly Leu Lys Pro Thr Val Ala Ala Ile Glu Ala Gly Lys Asp Ile
            180                 185                 190

Ala Leu Ala Asn Lys Glu Thr Met Ile Ala Gly Ala Pro Phe Val Leu
        195                 200                 205

Pro Leu Ala His Lys His Asn Ile Lys Ile Leu Pro Ala Asp Ser Glu
```

```
        210                 215                 220
His Ser Ala Ile Phe Gln Ser Ile Gln Gly Leu Pro Lys Gly Ala Leu
225                 230                 235                 240

Arg Lys Ile Leu Leu Thr Gly Ser Gly Gly Ala Phe Arg Glu Trp Pro
                245                 250                 255

Ala Glu Lys Met Lys Asp Ile Lys Leu Ala Asp Ala Leu Lys His Pro
            260                 265                 270

Ile Trp Ser Leu Gly Arg Lys Ile Thr Ile Asp Ser Ala Thr Leu Phe
        275                 280                 285

Asn Lys Gly Leu Glu Val Ile Glu Ala His Tyr Leu Phe Gly Ala Ser
    290                 295                 300

Tyr Asp Asp Ile Glu Ile Val Ile His Pro Gln Ser Ile Ile His Ser
305                 310                 315                 320

Leu Val Glu Thr Xaa Asp Ser Ser Val Asn Ala Gln Leu Gly Ile Pro
                325                 330                 335

Asp Met Arg Leu Pro Leu Leu Tyr Thr Leu Ser Trp Pro Glu Arg Ile
                340                 345                 350

Tyr Cys Ser Glu Val Thr Trp Pro Arg Leu Asp Leu Ser Lys Tyr Gly
            355                 360                 365

Ser Leu Thr Phe Tyr Ala Pro Asp Asp Lys Lys Phe Pro Ser Val Asn
        370                 375                 380

Leu Cys Tyr Ala Ala Gly Arg Ala Gly Gly Thr Met Thr Gly Val Leu
385                 390                 395                 400

Ser Ala Ala Asn Glu Lys Ala Val Glu Met Phe Val Glu Lys Ile
                405                 410                 415

Ser Tyr Leu Asp Ile Phe Lys Val Val Glu Leu Thr Cys Gln Glu His
                420                 425                 430

Gln Lys Glu Leu Val Ala Ser Pro Ser Leu Glu Glu Ile Ile His Tyr
            435                 440                 445

Asp Gln Trp Ala Arg Gln Tyr Ala Ala Ser Leu Gln Lys Xaa Phe Lys
        450                 455                 460

Cys Leu Asn Pro Ile Phe Leu Thr Tyr Phe Arg Ser Trp Gly Cys Gly
465                 470                 475                 480

Gly Leu Leu Ala Thr Ala Ser Ile Phe Cys Lys Cys Ile Val Gly Ser
                485                 490                 495

Ser Ile Leu

<210> SEQ ID NO 9
<211> LENGTH: 784
<212> TYPE: DNA
<213> ORGANISM: Glycine max
<220> FEATURE:
<221> NAME/KEY: unsure
<222> LOCATION: (55)
<223> OTHER INFORMATION: n = A, C, G, or T
<220> FEATURE:
<221> NAME/KEY: unsure
<222> LOCATION: (100)
<223> OTHER INFORMATION: n = A, C, G, or T
<220> FEATURE:
<221> NAME/KEY: unsure
<222> LOCATION: (109)
<223> OTHER INFORMATION: n = A, C, G, or T
<220> FEATURE:
<221> NAME/KEY: unsure
<222> LOCATION: (120)
<223> OTHER INFORMATION: n = A, C, G, or T
<220> FEATURE:
<221> NAME/KEY: unsure
<222> LOCATION: (659)
<223> OTHER INFORMATION: n = A, C, G, or T
```

```
<220> FEATURE:
<221> NAME/KEY: unsure
<222> LOCATION: (675)
<223> OTHER INFORMATION: n = A, C, G, or T
<220> FEATURE:
<221> NAME/KEY: unsure
<222> LOCATION: (721)
<223> OTHER INFORMATION: n = A, C, G, or T
<220> FEATURE:
<221> NAME/KEY: unsure
<222> LOCATION: (735)
<223> OTHER INFORMATION: n = A, C, G, or T
<220> FEATURE:
<221> NAME/KEY: unsure
<222> LOCATION: (740)
<223> OTHER INFORMATION: n = A, C, G, or T
<220> FEATURE:
<221> NAME/KEY: unsure
<222> LOCATION: (743)
<223> OTHER INFORMATION: n = A, C, G, or T
<220> FEATURE:
<221> NAME/KEY: unsure
<222> LOCATION: (756)
<223> OTHER INFORMATION: n = A, C, G, or T
<220> FEATURE:
<221> NAME/KEY: unsure
<222> LOCATION: (772)
<223> OTHER INFORMATION: n = A, C, G, or T
<220> FEATURE:
<221> NAME/KEY: unsure
<222> LOCATION: (779)..(780)
<223> OTHER INFORMATION: n = A, C, G, or T

<400> SEQUENCE: 9
gcacgggttt attgctcagt gcaggcaaca ccaccaccac cagcctggcc gggangagcg      60
gttccggaac aaggtcgcaa gacttgggat ggaccaaaan ccatttcant tgtgggagn      120
actggttcaa ttggaactca gacactagat attgtggcag agaatccaga taagtttaaa     180
gttgtggcac ttgcagctgg ttcaaatgtt actcttcttg cagaccaggt aaaaagattt     240
aagcctcaac ttgttgctgt tagaaatgag tccctaattg ctgaacttga agaggccttg     300
catgatgttg aagaaaaacc tgagatcatc cctggagagc agggaatcat tgaggttgct     360
cgtcacccag atgcagttag tgtagtcaca ggaatagtag gctgtgcagg actgaagcca     420
acagttgcag cgatagaagc agggaaagac atagctttgg ccaacaaaga gacattgatt     480
gctggaggtc ctttgttctc ctcttgctca gaagcataat gtaaaaatac ttccagctga     540
ttcagaacat ctgccatctt tcagtgtatc caggggttgc cagagggtgc acttaggaga     600
gttattttaa ctgcatctgg aggtgctttc aggggatggc cagttggata actgaagang     660
ttaaagttgc tgatncatta aaacatccta ctggaatatg ggggaaagaa ctgtggactc     720
ngcaaccttt taanaaggn canaagtaaa tgagcncata ctgtttgggg cngctaagnn     780
catt                                                                 784

<210> SEQ ID NO 10
<211> LENGTH: 215
<212> TYPE: PRT
<213> ORGANISM: Glycine max
<220> FEATURE:
<221> NAME/KEY: UNSURE
<222> LOCATION: (19)
<223> OTHER INFORMATION: Xaa = ANY AMINO ACID
<220> FEATURE:
<221> NAME/KEY: UNSURE
<222> LOCATION: (183)
<223> OTHER INFORMATION: Xaa = ANY AMINO ACID

<400> SEQUENCE: 10

Ala Arg Val Tyr Cys Ser Val Gln Ala Thr Pro Pro Pro Ala Trp
```

```
            1               5                  10                 15
Pro Gly Xaa Ala Val Pro Glu Gln Gly Arg Lys Thr Trp Asp Gly Pro
                    20                  25                  30

Lys Pro Ile Ser Ile Val Gly Ser Thr Gly Ser Ile Gly Thr Gln Thr
                35                  40                  45

Leu Asp Ile Val Ala Glu Asn Pro Asp Lys Phe Lys Val Val Ala Leu
            50                  55                  60

Ala Ala Gly Ser Asn Val Thr Leu Leu Ala Asp Gln Val Lys Arg Phe
65                  70                  75                  80

Lys Pro Gln Leu Val Ala Val Arg Asn Glu Ser Leu Ile Ala Glu Leu
                85                  90                  95

Glu Glu Ala Leu His Asp Val Glu Lys Pro Glu Ile Ile Pro Gly
            100                 105                 110

Glu Gln Gly Ile Ile Glu Val Ala Arg His Pro Asp Ala Val Ser Val
                115                 120                 125

Val Thr Gly Ile Val Gly Cys Ala Gly Leu Lys Pro Thr Val Ala Ala
            130                 135                 140

Ile Glu Ala Gly Lys Asp Ile Ala Leu Ala Asn Lys Glu Thr Leu Ile
145                 150                 155                 160

Ala Gly Gly Pro Leu Ser Pro Leu Ala Gln Lys His Asn Val Lys Ile
                165                 170                 175

Leu Pro Ala Asp Ser Asp Xaa Ser Ala Ile Phe Gln Cys Ile Gln Gly
            180                 185                 190

Leu Pro Glu Gly Ala Leu Arg Arg Val Ile Leu Thr Ala Ser Gly Gly
                195                 200                 205

Ala Phe Arg Gly Trp Pro Val
    210                 215

<210> SEQ ID NO 11
<211> LENGTH: 642
<212> TYPE: DNA
<213> ORGANISM: Triticum aestivum
<220> FEATURE:
<221> NAME/KEY: unsure
<222> LOCATION: (506)
<223> OTHER INFORMATION: n = A, C, G, or T
<220> FEATURE:
<221> NAME/KEY: unsure
<222> LOCATION: (516)
<223> OTHER INFORMATION: n = A, C, G, or T
<220> FEATURE:
<221> NAME/KEY: unsure
<222> LOCATION: (534)
<223> OTHER INFORMATION: n = A, C, G, or T
<220> FEATURE:
<221> NAME/KEY: unsure
<222> LOCATION: (554)
<223> OTHER INFORMATION: n = A, C, G, or T
<220> FEATURE:
<221> NAME/KEY: unsure
<222> LOCATION: (576)
<223> OTHER INFORMATION: n = A, C, G, or T
<220> FEATURE:
<221> NAME/KEY: unsure
<222> LOCATION: (584)
<223> OTHER INFORMATION: n = A, C, G, or T
<220> FEATURE:
<221> NAME/KEY: unsure
<222> LOCATION: (597)
<223> OTHER INFORMATION: n = A, C, G, or T
<220> FEATURE:
<221> NAME/KEY: unsure
<222> LOCATION: (601)
<223> OTHER INFORMATION: n = A, C, G, or T
<220> FEATURE:
<221> NAME/KEY: unsure
```

<222> LOCATION: (606)
<223> OTHER INFORMATION: n = A, C, G, or T
<220> FEATURE:
<221> NAME/KEY: unsure
<222> LOCATION: (625)
<223> OTHER INFORMATION: n = A, C, G, or T
<220> FEATURE:
<221> NAME/KEY: unsure
<222> LOCATION: (628)
<223> OTHER INFORMATION: n = A, C, G, or T

<400> SEQUENCE: 11

```
ctccttctcc ctcctcgagc tctcctccgg caccaccagg agcaggaggg gagccgcctt      60
ccgcccccgc cagcaccagc gcaaagtcga cttcacatat caaaggaggg acaaaagagc     120
tgcctacctg aggacatgct gctccatgca gcagggccca ccgcccgcct ggccaggccg     180
agccgtcgtg gaacctgaga ggaggtcgtg ggagggcccc aagcccatct ccatcgtcgg     240
ctcaaccggt tccataggaa cacagacatt ggacatcgtt gcggagaacc tgacaagttc     300
ccgggttgtc gccttgctg ctgggtccaa cgtcactcct ctagctgata aggtgaaaac     360
gttcaaacca aactgggtgg tgttaagaaa cgatccatta cttaacgagc taaggaagc     420
attaactggt tgtgaaagag atccggatta tccctgggga caagtgcata gaggcgcacc     480
caccccggacc attacatcct acggnatat aggttncaag atcaacctac attncaacat     540
ttaactggaa aatntgcttt gggaacaaaa accttccag gtgnccttct ctccctncca     600
naacanattg aaatactctg cgatnaanat ctgatatcat ga                        642
```

<210> SEQ ID NO 12
<211> LENGTH: 94
<212> TYPE: PRT
<213> ORGANISM: Triticum aestivum

<400> SEQUENCE: 12

```
Met Gln Gln Gly Pro Pro Ala Trp Pro Gly Arg Ala Val Val Glu
  1               5                  10                  15

Pro Glu Arg Arg Ser Trp Glu Gly Pro Lys Pro Ile Ser Ile Val Gly
             20                  25                  30

Ser Thr Gly Ser Ile Gly Thr Gln Thr Leu Asp Ile Val Ala Glu Asn
         35                  40                  45

Leu Thr Ser Ser Arg Val Val Ala Leu Ala Ala Gly Ser Asn Val Thr
     50                  55                  60

Pro Leu Ala Asp Lys Val Lys Thr Phe Lys Pro Asn Trp Val Val Leu
 65                  70                  75                  80

Arg Asn Asp Pro Leu Leu Asn Glu Leu Lys Glu Ala Leu Thr
                 85                  90
```

<210> SEQ ID NO 13
<211> LENGTH: 360
<212> TYPE: DNA
<213> ORGANISM: Triticum aestivum
<220> FEATURE:
<221> NAME/KEY: unsure
<222> LOCATION: (295)
<223> OTHER INFORMATION: n = A, C, G, or T
<220> FEATURE:
<221> NAME/KEY: unsure
<222> LOCATION: (299)
<223> OTHER INFORMATION: n = A, C, G, or T
<220> FEATURE:
<221> NAME/KEY: unsure
<222> LOCATION: (313)
<223> OTHER INFORMATION: n = A, C, G, or T
<220> FEATURE:
<221> NAME/KEY: unsure

```
<222> LOCATION: (338)
<223> OTHER INFORMATION: n = A, C, G, or T
<220> FEATURE:
<221> NAME/KEY: unsure
<222> LOCATION: (352)
<223> OTHER INFORMATION: n = A, C, G, or T

<400> SEQUENCE: 13
catctgtcct ggctcagctg ggatggcctg acatgcggct accaatccta tacaccttgt      60
cttggccaga tagagtctac tgctccgagg tcacctggcc tcggctagat ctttgcaagc     120
tgggctcgct gacattcaaa gctcccgaca acgtgaaata cccatcggta gatctccgcc     180
gtacgcggca gggcgagccg ggggcaccat gacgggattt ttgagtgctg ctaatgagaa     240
ggcgtggagc ttgttcatcg acgaaaagat taactacctt ggacatcttc aaggngggng     300
agaatacctt ttnacgccaa ccgcaacaac tgggtganag ctcctcccca angggggggg     360

<210> SEQ ID NO 14
<211> LENGTH: 93
<212> TYPE: PRT
<213> ORGANISM: Triticum aestivum
<220> FEATURE:
<221> NAME/KEY: UNSURE
<222> LOCATION: (59)
<223> OTHER INFORMATION: Xaa = ANY AMINO ACID
<220> FEATURE:
<221> NAME/KEY: UNSURE
<222> LOCATION: (60)
<223> OTHER INFORMATION: Xaa = ANY AMINO ACID

<400> SEQUENCE: 14

Ser Val Leu Ala Gln Leu Gly Trp Pro Asp Met Arg Leu Pro Ile Leu
  1               5                  10                  15

Tyr Thr Leu Ser Trp Pro Asp Arg Val Tyr Cys Ser Glu Val Thr Trp
             20                  25                  30

Pro Arg Leu Asp Leu Cys Lys Leu Gly Ser Leu Thr Phe Lys Ala Pro
         35                  40                  45

Asp Asn Val Lys Tyr Pro Ser Val Asp Leu Xaa Xaa Tyr Ala Ala Gly
     50                  55                  60

Arg Ala Gly Gly Thr Met Thr Gly Phe Leu Ser Ala Ala Asn Glu Lys
 65                  70                  75                  80

Ala Trp Ser Leu Phe Ile Asp Glu Lys Ile Asn Tyr Leu
             85                  90

<210> SEQ ID NO 15
<211> LENGTH: 1847
<212> TYPE: DNA
<213> ORGANISM: Zea mays
<220> FEATURE:
<221> NAME/KEY: unsure
<222> LOCATION: (5)..(9)
<223> OTHER INFORMATION: n = A, C, G, or T

<400> SEQUENCE: 15
aatgnnnnna tcaggctgtt acataggggg gcttgcattg tacacaccca acctggccta      60
gcctacccta ctacactcgt gccgattcgg cacgagcagc gacggtcgcc accaccgctc     120 ccctcccctct cccccctcctc gcccagcggc aattaccaca gcctcccccag caagccggga     180 tggctgcact caaggcatcg ttccggggtg agctcagcgc cgcttccttc ctcgactcca     240
gcaggggacc tctcgtccag cacaaagtgg attttacgtt tcaaaggaag gcaaacgag     300 ctatttcact gagaaggaca tgctgttcta tgcaacaggc tccaccacca gcatggcctg     360
ggcgagctgt tgctgagcct ggccggaggt catgggatgg cccaaagcct atctcgattg     420
```

```
ttggttcaac tggttccata ggaacacaga cattggacat tgttgcggag aatcctgata      480
agttcagagt tgttgctctt gctgctggat ccaatgtcac gcttctagct gatcaggtca      540
aaacattcaa acctaagttg gttgctgtaa gaaacgaatc attagttgat gaattgaaag      600
aagccttggc tgattgcgaa gagaagccag aaattattcc tggggagcaa ggtgtcatag      660
aagttgctcg ccatccagat gcagttacag ttgtcacagg gatagtaggt tgtgcagggc      720
tgaagcctac agttgctgca attgaagctg gtaaagacat agcattggca aacaaagaga      780
cacttattgc aggtggtcct tttgtgcttc cccttgcaca caaacacaaa gtgaaaattc      840
ttccagctga ttctgagcac tctgcaatat ttcagtgtat acaaggcttg tccgaaggtg      900
cacttcgtcg cattattcta actgcatcag gtggtgcttt cagggactgg ccagttgaca      960
ggctgaaaga tgtaaaagtt gctgacgctt taaagcatcc aaactggaat atgggaagga     1020
agatcacagt agattctgct actttattca acaagggttt agaagttatt gaagcacatt     1080
atttatttgg tgctgaatat gatgacattg agattgtgat tcacccacag tctatcatac     1140
actctatggt tgaaacccag gattcatctg tcctagctca gttgggatgg ccagatatgc     1200
ggttaccaat cttatacacc ttatcatggc cagatagaat ctattgctct gaggtcacct     1260
ggccccgtct ggatctttgc aagttgggtt cactgacatt cagagctcca gacaacgtaa     1320
aatacccatc aatggaccta gcctatgcag ctggccgcgc tggggcacc atgacaggag      1380 tcctgagcgc tgctaatgag aaggccgtgg agttgttcat tgacgagaag attagctacc     1440
tggacatatt caaggtggtg gagcttacat gtaacgcgca tcggaacgag ctggtaacaa     1500
gcccgtcact ggaggagatc gtccattacg atctgtgggc gaggagatat gcagccagtc     1560
tacaaccatc ttctggcctg agccctgtcc ctgcataata ggtcgtcacg acaacgttgt     1620
acagcaggag ttctaagata tgatgtgttt gtggctcctg tttccatgtt caattttcag     1680
gcctccacat gaataaaatg catctattcc atgtgatttc ttttatggat gaagtgtgcg     1740
aagtcgggtg ggaatcagat gcatcccttt cggtggagtt cttacgtagg gttgagcagc     1800 atttttaaa aaggtttttt tacctctgca aaaaaaaaa aaaaaaa                     1847
```

<210> SEQ ID NO 16
<211> LENGTH: 472
<212> TYPE: PRT
<213> ORGANISM: Zea mays

<400> SEQUENCE: 16

```
Met Ala Ala Leu Lys Ala Ser Phe Arg Gly Glu Leu Ser Ala Ala Ser
 1               5                  10                  15

Phe Leu Asp Ser Ser Arg Gly Pro Leu Val Gln His Lys Val Asp Phe
            20                  25                  30

Thr Phe Gln Arg Lys Gly Lys Arg Ala Ile Ser Leu Arg Arg Thr Cys
        35                  40                  45

Cys Ser Met Gln Gln Ala Pro Pro Ala Trp Pro Gly Arg Ala Val
    50                  55                  60

Ala Glu Pro Gly Arg Arg Ser Trp Asp Gly Pro Lys Pro Ile Ser Ile
65                  70                  75                  80

Val Gly Ser Thr Gly Ser Ile Gly Thr Gln Thr Leu Asp Ile Val Ala
                85                  90                  95

Glu Asn Pro Asp Lys Phe Arg Val Val Ala Leu Ala Ala Gly Ser Asn
            100                 105                 110

Val Thr Leu Leu Ala Asp Gln Val Lys Thr Phe Lys Pro Lys Leu Val
        115                 120                 125
```

Ala Val Arg Asn Glu Ser Leu Val Asp Glu Leu Lys Glu Ala Leu Ala
            130                 135                 140

Asp Cys Glu Glu Lys Pro Glu Ile Ile Pro Gly Gln Gly Val Ile
145                 150                 155                 160

Glu Val Ala Arg His Pro Asp Ala Val Thr Val Thr Gly Ile Val
                165                 170                 175

Gly Cys Ala Gly Leu Lys Pro Thr Val Ala Ala Ile Glu Ala Gly Lys
            180                 185                 190

Asp Ile Ala Leu Ala Asn Lys Glu Thr Leu Ile Ala Gly Pro Phe
            195                 200                 205

Val Leu Pro Leu Ala His Lys His Lys Val Lys Ile Leu Pro Ala Asp
210                 215                 220

Ser Glu His Ser Ala Ile Phe Gln Cys Ile Gln Gly Leu Ser Glu Gly
225                 230                 235                 240

Ala Leu Arg Arg Ile Ile Leu Thr Ala Ser Gly Gly Ala Phe Arg Asp
                245                 250                 255

Trp Pro Val Asp Arg Leu Lys Asp Val Lys Val Ala Asp Ala Leu Lys
                260                 265                 270

His Pro Asn Trp Asn Met Gly Arg Lys Ile Thr Val Asp Ser Ala Thr
            275                 280                 285

Leu Phe Asn Lys Gly Leu Glu Val Ile Glu Ala His Tyr Leu Phe Gly
290                 295                 300

Ala Glu Tyr Asp Asp Ile Glu Ile Val Ile His Pro Gln Ser Ile Ile
305                 310                 315                 320

His Ser Met Val Glu Thr Gln Asp Ser Ser Val Leu Ala Gln Leu Gly
                325                 330                 335

Trp Pro Asp Met Arg Leu Pro Ile Leu Tyr Thr Leu Ser Trp Pro Asp
            340                 345                 350

Arg Ile Tyr Cys Ser Glu Val Thr Trp Pro Arg Leu Asp Leu Cys Lys
            355                 360                 365

Leu Gly Ser Leu Thr Phe Arg Ala Pro Asp Asn Val Lys Tyr Pro Ser
370                 375                 380

Met Asp Leu Ala Tyr Ala Ala Gly Arg Ala Gly Gly Thr Met Thr Gly
385                 390                 395                 400

Val Leu Ser Ala Ala Asn Glu Lys Ala Val Glu Leu Phe Ile Asp Glu
                405                 410                 415

Lys Ile Ser Tyr Leu Asp Ile Phe Lys Val Val Glu Leu Thr Cys Asn
            420                 425                 430

Ala His Arg Asn Glu Leu Val Thr Ser Pro Ser Leu Glu Glu Ile Val
            435                 440                 445

His Tyr Asp Leu Trp Ala Arg Arg Tyr Ala Ala Ser Leu Gln Pro Ser
            450                 455                 460

Ser Gly Leu Ser Pro Val Pro Ala
465                 470

<210> SEQ ID NO 17
<211> LENGTH: 2019
<212> TYPE: DNA
<213> ORGANISM: Glycine max

<400> SEQUENCE: 17
gcagccacca ttattgttgt tattggagat tcaattctt tgtctttcaa actcctcaag     60
ttgggtttat gtgatgatgg ctctcaacat ctcttctcca gctgaagtca agtccatttt    120
tttcgctgat tccttcaagt ctaactgcct cacagcaaaa ttctcaggtg ggtttgcttt    180

```
taagagaaaa gagcgtagag cagcatctgg aggacgggtt tattgctcag tgcaggcaac      240
accaccacca ccagcctggc cgggacgagc ggttccggaa caaggtcgca agacttggga      300
tggaccaaaa cccatttcaa ttgtggggag tactggttca attggaactc agacactaga      360
tattgtggca gagaatccag ataagtttaa agttgtggca cttgcagctg gttcaaatgt      420
tactcttctt gcagaccagg taaaaagatt taagcctcaa cttgttgctg ttagaaatga      480
gtccctaatt gctgaacttg aagaggcctt gcatgatgtt gaagaaaaac ctgagatcat      540
ccctggagag cagggaatca ttgaggttgc tcgtcaccca gatgcagtta gtgtagtcac      600
aggaatagta ggctgtgcag gactgaagcc aacagttgca gcgatagaag cagggaaaga      660
catagctttg gccaacaaag agacattgat tgctggaggt cctttttgttc ttcctcttgc      720 tcagaagcat aatgtaaaaa acttccagc tgattcagaa cattctgcca tctttcagtg      780
tatccagggg ttgccagagg gtgcacttag gagagttatt ttaactgcat ctggaggtgc      840 tttcaggggat tggccagttg ataaactgaa agatgttaaa gttgctgatg cattaaaaca      900
tcctaactgg aatatgggga aaagataac tgtggactct gctaccctt ttaataaggg      960 tctagaagta attgaagcac attacttgtt tggagctgac tacgatcata ttgagattgt      1020
cattcatcca caatcaatca tacattcaat gattgaaaca caggattcat ctgttcttgc      1080
acaattgggg tggcctgata tgcgtttgcc aatcctctat acattatcat ggcctgacag      1140
gatttattgt tctgaagtca cttggccacg ccttgatctt tgcaagcttg gttcacttac      1200
atttaaaact ccagataatg taagtatcc atccatgaat cttgcatttt ctgctggccg      1260
tgctggaggc acaatgacag gagttcttag tgcagcaaat gaaaaagctg tagagatgtt      1320
tattgatgaa aagataagct attggaattt attcaaagtt gtggagctaa catgtgagaa      1380
gcatcaaaat gaattggtat cctctccttc ccttgaggaa attattcact atgacctgtg      1440
ggcgcgaaaa tatgctgcta gtctgcaaga ctcttccagc ttcactccta ttcttgcatg      1500
aggatgatta aactagggat gtggctgatg cttcccaatt gcctgctttc accataattt      1560
cttcgggcat tgaacaatgt agaatggtgc attccacaga tgttgaaaat taaataggtt      1620
ttttgtttat ggaatgttgg tgttttaaca cctttcaatt gatcttatag ttttgtcgta      1680
atttcatgaa aaacgatgtc ttttaatag tcaataggag cctaggaggt tggttggttg      1740
cctatgaatg tgtcaaagtc aagaagggga atggattttc tcatattcaa aatttacatg      1800
atgtggtcaa ctagaagttt tgtatttctc tttttctaat agaattaaat aggtggagtc      1860
ttacaaaaat taacagagat agacacaaaa gttgaccaat caccaatcac tttcataaaa      1920
ggattccttt tcttttttcct cagcacacat tcgttggctg atattattat atgaaattgg      1980
tattatttgg atatcatagc taaaaaaaaa aaaaaaaa                              2019

<210> SEQ ID NO 18
<211> LENGTH: 475
<212> TYPE: PRT
<213> ORGANISM: Glycine max

<400> SEQUENCE: 18

Met Met Ala Leu Asn Ile Ser Ser Pro Ala Glu Val Lys Ser Ile Phe
1               5                   10                  15

Phe Ala Asp Ser Phe Lys Ser Asn Cys Leu Thr Ala Lys Phe Ser Gly
                20                  25                  30

Gly Phe Ala Phe Lys Arg Lys Glu Arg Arg Ala Ala Ser Gly Gly Arg
            35                  40                  45
```

-continued

```
Val Tyr Cys Ser Val Gln Ala Thr Pro Pro Pro Ala Trp Pro Gly
 50                  55                  60

Arg Ala Val Pro Glu Gln Gly Arg Lys Thr Trp Asp Gly Pro Lys Pro
 65                  70                  75                  80

Ile Ser Ile Val Gly Ser Thr Gly Ser Ile Gly Thr Gln Thr Leu Asp
                 85                  90                  95

Ile Val Ala Glu Asn Pro Asp Lys Phe Lys Val Val Ala Leu Ala Ala
            100                 105                 110

Gly Ser Asn Val Thr Leu Leu Ala Asp Gln Val Lys Arg Phe Lys Pro
        115                 120                 125

Gln Leu Val Ala Val Arg Asn Glu Ser Leu Ile Ala Glu Leu Glu Glu
    130                 135                 140

Ala Leu His Asp Val Glu Glu Lys Pro Glu Ile Ile Pro Gly Glu Gln
145                 150                 155                 160

Gly Ile Ile Glu Val Ala Arg His Pro Asp Ala Val Ser Val Val Thr
                165                 170                 175

Gly Ile Val Gly Cys Ala Gly Leu Lys Pro Thr Val Ala Ala Ile Glu
            180                 185                 190

Ala Gly Lys Asp Ile Ala Leu Ala Asn Lys Glu Thr Leu Ile Ala Gly
        195                 200                 205

Gly Pro Phe Val Leu Pro Leu Ala Gln Lys His Asn Val Lys Ile Leu
    210                 215                 220

Pro Ala Asp Ser Glu His Ser Ala Ile Phe Gln Cys Ile Gln Gly Leu
225                 230                 235                 240

Pro Glu Gly Ala Leu Arg Arg Val Ile Leu Thr Ala Ser Gly Gly Ala
                245                 250                 255

Phe Arg Asp Trp Pro Val Asp Lys Leu Lys Asp Val Lys Val Ala Asp
            260                 265                 270

Ala Leu Lys His Pro Asn Trp Asn Met Gly Lys Lys Ile Thr Val Asp
        275                 280                 285

Ser Ala Thr Leu Phe Asn Lys Gly Leu Glu Val Ile Glu Ala His Tyr
    290                 295                 300

Leu Phe Gly Ala Asp Tyr Asp His Ile Glu Ile Val Ile His Pro Gln
305                 310                 315                 320

Ser Ile Ile His Ser Met Ile Glu Thr Gln Asp Ser Ser Val Leu Ala
                325                 330                 335

Gln Leu Gly Trp Pro Asp Met Arg Leu Pro Ile Leu Tyr Thr Leu Ser
            340                 345                 350

Trp Pro Asp Arg Ile Tyr Cys Ser Glu Val Thr Trp Pro Arg Leu Asp
        355                 360                 365

Leu Cys Lys Leu Gly Ser Leu Thr Phe Lys Thr Pro Asp Asn Val Lys
    370                 375                 380

Tyr Pro Ser Met Asn Leu Ala Phe Ser Ala Gly Arg Ala Gly Gly Thr
385                 390                 395                 400

Met Thr Gly Val Leu Ser Ala Ala Asn Glu Lys Ala Val Glu Met Phe
                405                 410                 415

Ile Asp Glu Lys Ile Ser Tyr Trp Asn Leu Phe Lys Val Val Glu Leu
            420                 425                 430

Thr Cys Glu Lys His Gln Asn Glu Leu Val Ser Ser Pro Ser Leu Glu
        435                 440                 445

Glu Ile Ile His Tyr Asp Leu Trp Ala Arg Lys Tyr Ala Ala Ser Leu
    450                 455                 460

Gln Asp Ser Ser Ser Phe Thr Pro Ile Leu Ala
465                 470                 475
```

<210> SEQ ID NO 19
<211> LENGTH: 1640
<212> TYPE: DNA
<213> ORGANISM: Triticum aestivum

<400> SEQUENCE: 19

```
gcacgagctc cttctccctc ctcgagctct cctccggcac caccaggagc aggaggggag    60
ccgccttccg cccccgccag caccagcgca aagtggactt gacgtttcaa aggagggaca   120
aaagagcagc ctacctgagg acatgctgct cgatgcagca gggcccaccg cccgcctggc   180
ctggccgagc cgtcgcggaa cccgagagga ggtcgtggga gggccccaag cccatctcga   240
tcgtcggctc aaccggttcc ataggaacac agacattgga catcgttgcg gagaatcctg   300
acaagttccg ggttgtcgct cttgctgctg gctccaatgt cactcttcta gctgatcagg   360
tgaaaacgtt caagccaaag ctggtggctg taagaaacga gtcattactt aacgagctaa   420
aggaagcgtt agctggttgt gaagaaatgc cggaaattat tcctggggag caaggtgtca   480
tagaggtcgc tcgccacccg gatgcagtta cagtcgttac gggcatagta gggtgtgcag   540
gactcaagcc tacagttgca gcaattgaag ctgggaaaga tattgcgttg gcgaacaaag   600
agacacttat cgcaggcggt ccgttcgtgc ttcccctgc gcacaagcac aatgtgaaaa   660
tacttcctgc tgattcagag cactctgcaa tatttcagtg tatacaaggc ttgtctgaag   720
gatcacttcg tcgcgttatt ctgactgcgt ctggcggtgc tttcagggac tggccagttg   780
agaagctgaa agatgtaaag gttgccgatg ctttgaagca cccaaactgg agcatgggga   840
agaaaatcac agtagattct gctactttgt tcaacaaggg gttagaagtt atcgaggcgc   900
attatttgtt tggtgctgaa tatgatgaca ttgagattgt gattcaccca cagtccatca   960
tacactctat gattgaaacc caggattcat ctgtcctggc tcagctggga tggccagaca  1020
tgcggctacc gatcctatac accttgtctt ggccagaccg agtctactgc tccgaggtca  1080
cctggccccg gctagacctt tgcaagctgg gttcgctgac atttaaagct cccgacaacg  1140
tgaaataccc atcggtggat ctcgcgtatg cggcagggcg ggccggggc accatgacgg  1200
gagttttgag tgctgctaat gagaaggcgg tggagctgtt catcgacgaa aagatcagct  1260
acctggacat cttcaaggtg gtggagatga cgtgcgacgc gcaccgcaac gagctggtga  1320
caaggccgtc gctcgaggag atcatacatt acgaccagtg ggcaaggaag tttgccgcca  1380
acctacagcc atcgtcgtct ggacggagcc ctgtgctcgc ctaaggccct tcttcctgga  1440
gctggccgat gaagcacaga agatgtagcc atggcctggc cttgctaaaa ctggccatgt  1500
ggaaaccaag cttagatatt tcaacaaggc acacataggt tgccttccag aaatgtaaat  1560
catgtgttgg cacgaataaa tcatgtaagt tttgatggat ggatgaaata ggcaaggaat  1620
caaaaaaaaa aaaaaaaaaa                                              1640
```

<210> SEQ ID NO 20
<211> LENGTH: 473
<212> TYPE: PRT
<213> ORGANISM: Triticum aestivum

<400> SEQUENCE: 20

Thr Ser Ser Phe Ser Leu Leu Glu Leu Ser Ser Gly Thr Thr Arg Ser
 1               5                  10                  15

Arg Arg Gly Ala Ala Phe Arg Pro Arg Gln His Gln Arg Lys Val Asp
            20                  25                  30

Leu Thr Phe Gln Arg Arg Asp Lys Arg Ala Ala Tyr Leu Arg Thr Cys

```
                  35                  40                  45
Cys Ser Met Gln Gln Gly Pro Pro Ala Trp Pro Gly Arg Ala Val
             50                  55                  60
Ala Glu Pro Glu Arg Arg Ser Trp Glu Gly Lys Pro Ile Ser Ile
 65                  70                  75                  80
Val Gly Ser Thr Gly Ser Ile Gly Thr Gln Thr Leu Asp Ile Val Ala
                 85                  90                  95
Glu Asn Pro Asp Lys Phe Arg Val Val Ala Leu Ala Ala Gly Ser Asn
            100                 105                 110
Val Thr Leu Leu Ala Asp Gln Val Lys Thr Phe Lys Pro Lys Leu Val
            115                 120                 125
Ala Val Arg Asn Glu Ser Leu Leu Asn Glu Leu Lys Glu Ala Leu Ala
            130                 135                 140
Gly Cys Glu Glu Met Pro Glu Ile Ile Pro Gly Glu Gln Gly Val Ile
145                 150                 155                 160
Glu Val Ala Arg His Pro Asp Ala Val Thr Val Thr Gly Ile Val
                165                 170                 175
Gly Cys Ala Gly Leu Lys Pro Thr Val Ala Ile Glu Ala Gly Lys
            180                 185                 190
Asp Ile Ala Leu Ala Asn Lys Glu Thr Leu Ile Ala Gly Gly Pro Phe
            195                 200                 205
Val Leu Pro Leu Ala His Lys His Asn Val Lys Ile Leu Pro Ala Asp
            210                 215                 220
Ser Glu His Ser Ala Ile Phe Gln Cys Ile Gln Gly Leu Ser Glu Gly
225                 230                 235                 240
Ser Leu Arg Arg Val Ile Leu Thr Ala Ser Gly Gly Ala Phe Arg Asp
                245                 250                 255
Trp Pro Val Glu Lys Leu Lys Asp Val Lys Val Ala Asp Ala Leu Lys
            260                 265                 270
His Pro Asn Trp Ser Met Gly Lys Lys Ile Thr Val Asp Ser Ala Thr
            275                 280                 285
Leu Phe Asn Lys Gly Leu Glu Val Ile Glu Ala His Tyr Leu Phe Gly
            290                 295                 300
Ala Glu Tyr Asp Asp Ile Glu Ile Val Ile His Pro Gln Ser Ile Ile
305                 310                 315                 320
His Ser Met Ile Glu Thr Gln Asp Ser Ser Val Leu Ala Gln Leu Gly
                325                 330                 335
Trp Pro Asp Met Arg Leu Pro Ile Leu Tyr Thr Leu Ser Trp Pro Asp
            340                 345                 350
Arg Val Tyr Cys Ser Glu Val Thr Trp Pro Arg Leu Asp Leu Cys Lys
            355                 360                 365
Leu Gly Ser Leu Thr Phe Lys Ala Pro Asp Asn Val Lys Tyr Pro Ser
            370                 375                 380
Val Asp Leu Ala Tyr Ala Ala Gly Arg Ala Gly Gly Thr Met Thr Gly
385                 390                 395                 400
Val Leu Ser Ala Ala Asn Glu Lys Ala Val Glu Leu Phe Ile Asp Glu
                405                 410                 415
Lys Ile Ser Tyr Leu Asp Ile Phe Lys Val Val Glu Met Thr Cys Asp
            420                 425                 430
Ala His Arg Asn Glu Leu Val Thr Arg Pro Ser Leu Glu Glu Ile Ile
            435                 440                 445
His Tyr Asp Gln Trp Ala Arg Lys Phe Ala Ala Asn Leu Gln Pro Ser
            450                 455                 460
```

Ser Ser Gly Arg Ser Pro Val Leu Ala
465                 470

<210> SEQ ID NO 21
<211> LENGTH: 406
<212> TYPE: PRT
<213> ORGANISM: Arabidopsis thaliana

<400> SEQUENCE: 21

Ala Pro Arg Gln Ser Trp Asp Gly Pro Lys Pro Ile Ser Ile Val Gly
1               5                   10                  15

Ser Thr Gly Ser Ile Gly Thr Gln Thr Leu Asp Ile Val Ala Glu Asn
            20                  25                  30

Pro Asp Lys Phe Arg Val Val Ala Leu Ala Ala Gly Ser Asn Val Thr
        35                  40                  45

Leu Leu Ala Asp Gln Val Arg Arg Phe Lys Pro Ala Leu Val Ala Val
    50                  55                  60

Arg Asn Glu Ser Leu Ile Asn Glu Leu Lys Glu Ala Leu Ala Asp Leu
65                  70                  75                  80

Asp Tyr Lys Leu Glu Ile Ile Pro Gly Glu Gln Gly Val Ile Glu Val
                85                  90                  95

Ala Arg His Pro Glu Ala Val Thr Val Val Thr Gly Ile Val Gly Cys
            100                 105                 110

Ala Gly Leu Lys Pro Thr Val Ala Ala Ile Glu Ala Gly Lys Asp Ile
        115                 120                 125

Ala Leu Ala Asn Lys Glu Thr Leu Ile Ala Gly Gly Pro Phe Val Leu
    130                 135                 140

Pro Leu Ala Asn Lys His Asn Val Lys Ile Leu Pro Ala Asp Ser Glu
145                 150                 155                 160

His Ser Ala Ile Phe Gln Cys Ile Gln Gly Leu Pro Glu Gly Ala Leu
                165                 170                 175

Arg Lys Ile Ile Leu Thr Ala Ser Gly Gly Ala Phe Arg Asp Trp Pro
            180                 185                 190

Val Glu Lys Leu Lys Glu Val Lys Val Ala Asp Ala Leu Lys His Pro
        195                 200                 205

Asn Trp Asn Met Gly Lys Lys Ile Thr Val Asp Ser Ala Thr Leu Phe
    210                 215                 220

Asn Lys Gly Leu Glu Val Ile Glu Ala His Tyr Leu Phe Gly Ala Glu
225                 230                 235                 240

Tyr Asp Asp Ile Glu Ile Val Ile His Pro Gln Ser Ile Ile His Ser
                245                 250                 255

Met Ile Glu Thr Gln Asp Ser Ser Val Leu Ala Gln Leu Gly Trp Pro
            260                 265                 270

Asp Met Arg Leu Pro Ile Leu Tyr Thr Met Ser Trp Pro Asp Arg Val
        275                 280                 285

Pro Cys Ser Glu Val Thr Trp Pro Arg Leu Asp Leu Cys Lys Leu Gly
    290                 295                 300

Ser Leu Thr Phe Lys Lys Pro Asp Asn Val Lys Tyr Pro Ser Met Asp
305                 310                 315                 320

Leu Ala Tyr Ala Ala Gly Arg Ala Gly Gly Thr Met Thr Gly Val Leu
                325                 330                 335

Ser Ala Ala Asn Glu Lys Ala Val Glu Met Phe Ile Asp Glu Lys Ile
            340                 345                 350

Ser Tyr Leu Asp Ile Phe Lys Val Val Glu Leu Thr Cys Asp Lys His
        355                 360                 365

```
Arg Asn Glu Leu Val Thr Ser Pro Ser Leu Glu Glu Ile Val His Tyr
            370                 375                 380

Asp Leu Trp Ala Arg Glu Tyr Ala Ala Asn Val Gln Leu Ser Ser Gly
385                 390                 395                 400

Ala Arg Pro Val His Ala
                405

<210> SEQ ID NO 22
<211> LENGTH: 475
<212> TYPE: PRT
<213> ORGANISM: Mentha x piperita

<400> SEQUENCE: 22

Met Ala Leu Asn Leu Met Ala Pro Thr Glu Ile Lys Thr Leu Ser Phe
1               5                   10                  15

Leu Asp Ser Ser Lys Ser Asn Tyr Asn Leu Asn Pro Leu Lys Phe Gln
            20                  25                  30

Gly Gly Phe Ala Phe Lys Arg Lys Asp Ser Arg Cys Thr Ala Ala Lys
        35                  40                  45

Arg Val His Cys Ser Ala Gln Ser Gln Ser Pro Pro Ala Trp Pro
50                  55                  60

Gly Arg Ala Phe Pro Glu Pro Gly Arg Met Thr Trp Glu Gly Pro Lys
65                  70                  75                  80

Pro Ile Ser Val Ile Gly Ser Thr Gly Ser Ile Gly Thr Gln Thr Leu
                85                  90                  95

Asp Ile Val Ala Glu Asn Pro Asp Lys Phe Arg Ile Val Ala Leu Ala
            100                 105                 110

Ala Gly Ser Asn Val Thr Leu Leu Ala Asp Gln Lys Ala Phe Lys Pro
        115                 120                 125

Lys Leu Val Ser Val Lys Asp Glu Ser Leu Ile Ser Glu Leu Lys Glu
130                 135                 140

Ala Leu Ala Gly Phe Glu Asp Met Pro Glu Ile Ile Pro Gly Glu Gln
145                 150                 155                 160

Gly Met Ile Glu Val Ala Arg His Pro Asp Ala Val Thr Val Val Thr
                165                 170                 175

Gly Ile Val Gly Cys Ala Gly Leu Lys Pro Thr Val Ala Ala Ile Glu
            180                 185                 190

Ala Gly Lys Asp Ile Ala Leu Ala Asn Lys Glu Thr Leu Ile Ala Gly
        195                 200                 205

Gly Pro Phe Val Leu Pro Leu Ala Lys Lys His Asn Val Lys Ile Leu
210                 215                 220

Pro Ala Asp Ser Glu His Ser Ala Ile Phe Gln Cys Ile Gln Gly Leu
225                 230                 235                 240

Pro Glu Gly Ala Leu Arg Arg Ile Ile Leu Thr Ala Ser Gly Gly Ala
                245                 250                 255

Phe Arg Asp Leu Pro Val Glu Lys Leu Lys Glu Val Lys Val Ala Asp
            260                 265                 270

Ala Leu Lys His Ser Asn Trp Asn Met Gly Lys Lys Asn Thr Val Arg
        275                 280                 285

Leu Leu Gln Leu Phe Phe Asn Lys Gly Leu Glu Val Ile Lys Ala His
290                 295                 300

Tyr Leu Phe Gly Ala Glu Tyr Asp Asp Ile Glu Val Ile Ile His Ser
305                 310                 315                 320

Pro Ser Ile Ile His Ser Met Val Glu Thr Gln Asp Ser Ser Val Leu
                325                 330                 335
```

```
Ala Gln Leu Gly Trp Pro Asp Met Arg Leu Pro Ile Leu Tyr Thr Leu
            340                 345                 350

Ser Trp Pro Glu Arg Val Tyr Cys Ser Glu Ile Thr Trp Pro Arg Leu
            355                 360                 365

Asp Leu Cys Lys Val Asp Leu Pro Phe Lys Pro Asp Asn Arg Glu
    370                 375                 380

Ile Pro Ala Met Asp Leu Ala Tyr Ala Ala Trp Lys Ser Arg Ser Thr
385                 390                 395                 400

Met Thr Gly Val Leu Ser Ala Ala Asn Glu Lys Ala Val Glu Met Phe
                405                 410                 415

Ile Asp Glu Lys Ile Gly Tyr Leu Asp Ile Phe Lys Val Val Glu Leu
            420                 425                 430

Thr Cys Asp Lys His Arg Ser Glu Met Ala Val Ser Pro Ser Leu Glu
            435                 440                 445

Glu Ile Val His Tyr Asp Gln Trp Ala Arg Asp Tyr Ala Ala Thr Val
            450                 455                 460

Leu Lys Ser Ala Gly Leu Ser Pro Ala Leu Val
465                 470                 475

<210> SEQ ID NO 23
<211> LENGTH: 1722
<212> TYPE: DNA
<213> ORGANISM: Glycine max
<220> FEATURE:
<221> NAME/KEY: CDS
<222> LOCATION: (12)..(1409)

<400> SEQUENCE: 23
caactgaggt g atg gct ttg aat ttg cct tct ccc gcc caa gtg aag ccc       50
            Met Ala Leu Asn Leu Pro Ser Pro Ala Gln Val Lys Pro
            1               5                   10 tta ttt ttc tct tca aat aac tcc aca aaa ctt cca ggt agc ttt tct       98
Leu Phe Phe Ser Ser Asn Asn Ser Thr Lys Leu Pro Gly Ser Phe Ser
    15                  20                  25 ttg aag aga aaa gat agt gac aca aca gta gag aga cga gtt tat tgc      146
Leu Lys Arg Lys Asp Ser Asp Thr Thr Val Glu Arg Arg Val Tyr Cys
30              35                  40                  45 tct gcc gct gct caa tca cca cca cca gca tgg cca gga aca gct att      194
Ser Ala Ala Ala Gln Ser Pro Pro Pro Ala Trp Pro Gly Thr Ala Ile
                50                  55                  60 ccc gag cct tct gat ttc aag aca tgg gat ggg caa aaa cct att tct      242
Pro Glu Pro Ser Asp Phe Lys Thr Trp Asp Gly Gln Lys Pro Ile Ser
            65                  70                  75 gtc tta gga tct acg ggt tca att gga act cag aca ctg agt ata gtg      290
Val Leu Gly Ser Thr Gly Ser Ile Gly Thr Gln Thr Leu Ser Ile Val
        80                  85                  90 gct gag ttc cca gaa aga ttt aaa gtt gtg agc ctt gct gct ggc tct      338
Ala Glu Phe Pro Glu Arg Phe Lys Val Val Ser Leu Ala Ala Gly Ser
    95                  100                 105 aat att act ctt ctt gct gac cag att aaa aca ttt aag cct gaa gtt      386
Asn Ile Thr Leu Leu Ala Asp Gln Ile Lys Thr Phe Lys Pro Glu Val
110             115                 120                 125 gtt ggt ctt aga aat gag tct tta att gat gaa ctc aaa gag gct ttg      434
Val Gly Leu Arg Asn Glu Ser Leu Ile Asp Glu Leu Lys Glu Ala Leu
                130                 135                 140 gct gat gtg gat cac aaa ccc gaa atc atc cct gga gag caa gga gtc      482
Ala Asp Val Asp His Lys Pro Glu Ile Ile Pro Gly Glu Gln Gly Val
            145                 150                 155 att gag gcc gct cgt cac cct gat gcc acc act gta gtt aca ggc ata      530
Ile Glu Ala Ala Arg His Pro Asp Ala Thr Thr Val Val Thr Gly Ile
```

```
                160             165             170
gtt ggt tgt gca gga tta aag cca aca gtt gca gca att gaa gca ggg      578
Val Gly Cys Ala Gly Leu Lys Pro Thr Val Ala Ala Ile Glu Ala Gly
175             180             185 aaa gac ata gca ttg gcc aac aaa gag aca atg att gcg gga gcc cct      626
Lys Asp Ile Ala Leu Ala Asn Lys Glu Thr Met Ile Ala Gly Ala Pro
190             195             200             205 ttt gtt ctt cct ctt gct cac aaa cat aac ata aaa att ctt ccc gct      674
Phe Val Leu Pro Leu Ala His Lys His Asn Ile Lys Ile Leu Pro Ala
        210             215             220 gat tcg gaa cat tct gca att ttt cag tct atc cag ggg ttg cca aag      722
Asp Ser Glu His Ser Ala Ile Phe Gln Ser Ile Gln Gly Leu Pro Lys
            225             230             235 ggt gca ctt agg aaa atc ctt tta act gga tca gga ggt gct ttc aga      770
Gly Ala Leu Arg Lys Ile Leu Leu Thr Gly Ser Gly Gly Ala Phe Arg
            240             245             250 gaa tgg cct gct gaa aag atg aaa gat att aag ctt gct gat gca tta      818
Glu Trp Pro Ala Glu Lys Met Lys Asp Ile Lys Leu Ala Asp Ala Leu
255             260             265 aag cat ccc ata tgg agt ttg ggg aga aaa ata act att gac tct gct      866
Lys His Pro Ile Trp Ser Leu Gly Arg Lys Ile Thr Ile Asp Ser Ala
270             275             280             285 acc ctt ttc aat aag ggt cta gaa gta att gaa gca cat tac ttg ttt      914
Thr Leu Phe Asn Lys Gly Leu Glu Val Ile Glu Ala His Tyr Leu Phe
            290             295             300 gga gca agc tat gac gat att gag att gtt att cat cct caa tct atc      962
Gly Ala Ser Tyr Asp Asp Ile Glu Ile Val Ile His Pro Gln Ser Ile
            305             310             315 ata cat tcc ttg gtt gaa acg cag gat tca tct gtt att gca cag ttg     1010
Ile His Ser Leu Val Glu Thr Gln Asp Ser Ser Val Ile Ala Gln Leu
            320             325             330 ggg ata cct gac atg cgc tta ccg ctc ctt tat aca tta tct tgg cca     1058
Gly Ile Pro Asp Met Arg Leu Pro Leu Leu Tyr Thr Leu Ser Trp Pro
335             340             345 gaa aga atc tat tgc tct gaa gta act tgg cct cgt ctt gat ctt agc     1106
Glu Arg Ile Tyr Cys Ser Glu Val Thr Trp Pro Arg Leu Asp Leu Ser
350             355             360             365 aag tat ggt tct cta aca ttt tat gca ccg gat gac aag aag ttt cca     1154
Lys Tyr Gly Ser Leu Thr Phe Tyr Ala Pro Asp Asp Lys Lys Phe Pro
        370             375             380 tcg gtg aat ctt tgc tat gct gcg gga cgt gct gga ggc acc atg aca     1202
Ser Val Asn Leu Cys Tyr Ala Ala Gly Arg Ala Gly Gly Thr Met Thr
            385             390             395 gga gtt ctt agt gca gca aat gag aaa gct gta gaa atg ttt gtt gaa     1250
Gly Val Leu Ser Ala Ala Asn Glu Lys Ala Val Glu Met Phe Val Glu
            400             405             410 gaa aag att agt tat ctg gat ata ttc aag gtt gtg gaa cta act tgt     1298
Glu Lys Ile Ser Tyr Leu Asp Ile Phe Lys Val Val Glu Leu Thr Cys
415             420             425 cag gaa cat caa aag gaa tta gta gca tct ccg tca ctc gaa gaa att     1346
Gln Glu His Gln Lys Glu Leu Val Ala Ser Pro Ser Leu Glu Glu Ile
430             435             440             445 att cac tat gac caa tgg gct cga caa tat gct gct agt ctg caa aaa     1394
Ile His Tyr Asp Gln Trp Ala Arg Gln Tyr Ala Ala Ser Leu Gln Lys
            450             455             460 gct tca agt gtt tga atcccatatt tctgacatat tttagaagtt ggggctgtgg     1449
Ala Ser Ser Val
            465 tggattgttg gcaactgcta gcatattttg taaatgtatt tgttggttca tcaatcttgt   1509
```

-continued

```
aaaatgtaaa ggggtagcta tataaagtat atgtactcct aaaagggttt caataaaagt    1569
tctagcttca gaataccatg ttttgagatg ctaatgcaac ctaggcagta cttttgtaat    1629
gctataattt tcctaattgt gtggttaagt gattaattca agatgcaaag gaaataaaat    1689
ttaaaattat gttaaaaaaa aaaaaaaaaa aaa                                 1722
```

<210> SEQ ID NO 24
<211> LENGTH: 465
<212> TYPE: PRT
<213> ORGANISM: Glycine max

<400> SEQUENCE: 24

```
Met Ala Leu Asn Leu Pro Ser Pro Ala Gln Val Lys Pro Leu Phe Phe
  1               5                  10                  15

Ser Ser Asn Asn Ser Thr Lys Leu Pro Gly Ser Phe Ser Leu Lys Arg
                 20                  25                  30

Lys Asp Ser Asp Thr Thr Val Glu Arg Arg Val Tyr Cys Ser Ala Ala
             35                  40                  45

Ala Gln Ser Pro Pro Ala Trp Pro Gly Thr Ala Ile Pro Glu Pro
         50                  55                  60

Ser Asp Phe Lys Thr Trp Asp Gly Gln Lys Pro Ile Ser Val Leu Gly
 65                  70                  75                  80

Ser Thr Gly Ser Ile Gly Thr Gln Thr Leu Ser Ile Val Ala Glu Phe
                 85                  90                  95

Pro Glu Arg Phe Lys Val Val Ser Leu Ala Ala Gly Ser Asn Ile Thr
            100                 105                 110

Leu Leu Ala Asp Gln Ile Lys Thr Phe Lys Pro Glu Val Val Gly Leu
        115                 120                 125

Arg Asn Glu Ser Leu Ile Asp Glu Leu Lys Glu Ala Leu Ala Asp Val
    130                 135                 140

Asp His Lys Pro Glu Ile Ile Pro Gly Glu Gln Gly Val Ile Glu Ala
145                 150                 155                 160

Ala Arg His Pro Asp Ala Thr Thr Val Val Thr Gly Ile Val Gly Cys
                165                 170                 175

Ala Gly Leu Lys Pro Thr Val Ala Ala Ile Glu Ala Gly Lys Asp Ile
            180                 185                 190

Ala Leu Ala Asn Lys Glu Thr Met Ile Ala Gly Ala Pro Phe Val Leu
        195                 200                 205

Pro Leu Ala His Lys His Asn Ile Lys Ile Leu Pro Ala Asp Ser Glu
    210                 215                 220

His Ser Ala Ile Phe Gln Ser Ile Gln Gly Leu Pro Lys Gly Ala Leu
225                 230                 235                 240

Arg Lys Ile Leu Leu Thr Gly Ser Gly Gly Ala Phe Arg Glu Trp Pro
                245                 250                 255

Ala Glu Lys Met Lys Asp Ile Lys Leu Ala Asp Ala Leu Lys His Pro
            260                 265                 270

Ile Trp Ser Leu Gly Arg Lys Ile Thr Ile Asp Ser Ala Thr Leu Phe
        275                 280                 285

Asn Lys Gly Leu Glu Val Ile Glu Ala His Tyr Leu Phe Gly Ala Ser
    290                 295                 300

Tyr Asp Asp Ile Glu Ile Val Ile His Pro Gln Ser Ile Ile His Ser
305                 310                 315                 320

Leu Val Glu Thr Gln Asp Ser Ser Val Ile Ala Gln Leu Gly Ile Pro
                325                 330                 335

Asp Met Arg Leu Pro Leu Leu Tyr Thr Leu Ser Trp Pro Glu Arg Ile
```

```
                340             345             350
Tyr Cys Ser Glu Val Thr Trp Pro Arg Leu Asp Leu Ser Lys Tyr Gly
            355             360             365

Ser Leu Thr Phe Tyr Ala Pro Asp Asp Lys Lys Phe Pro Ser Val Asn
    370             375             380

Leu Cys Tyr Ala Ala Gly Arg Ala Gly Gly Thr Met Thr Gly Val Leu
385             390             395             400

Ser Ala Ala Asn Glu Lys Ala Val Glu Met Phe Val Glu Glu Lys Ile
            405             410             415

Ser Tyr Leu Asp Ile Phe Lys Val Val Glu Leu Thr Cys Gln Glu His
            420             425             430

Gln Lys Glu Leu Val Ala Ser Pro Ser Leu Glu Glu Ile Ile His Tyr
            435             440             445

Asp Gln Trp Ala Arg Gln Tyr Ala Ala Ser Leu Gln Lys Ala Ser Ser
            450             455             460

Val
465

<210> SEQ ID NO 25
<211> LENGTH: 470
<212> TYPE: PRT
<213> ORGANISM: Mentha x piperita

<400> SEQUENCE: 25

Met Ala Pro Thr Glu Ile Lys Thr Leu Ser Phe Leu Asp Ser Ser Lys
1               5                   10                  15

Ser Asn Tyr Asn Leu Asn Pro Leu Lys Phe Gln Gly Gly Phe Ala Phe
            20                  25                  30

Lys Arg Lys Asp Ser Gly Cys Thr Ala Ala Lys Arg Val His Cys Ser
        35                  40                  45

Ala Gln Ser Gln Ser Pro Pro Pro Ala Trp Pro Gly Arg Ala Phe Pro
    50                  55                  60

Glu Pro Gly Arg Met Thr Trp Glu Gly Pro Lys Pro Ile Ser Val Ile
65                  70                  75                  80

Gly Ser Thr Gly Ser Ile Gly Thr Gln Thr Leu Asp Ile Val Ala Glu
                85                  90                  95

Asn Pro Asp Lys Phe Arg Ile Val Ala Leu Ala Ala Gly Ser Asn Val
            100                 105                 110

Thr Leu Leu Ala Asp Gln Val Lys Ala Phe Lys Pro Lys Leu Val Ser
        115                 120                 125

Val Lys Asp Glu Ser Leu Ile Ser Glu Leu Lys Glu Ala Leu Ala Gly
    130                 135                 140

Phe Glu Asp Met Pro Glu Ile Ile Pro Gly Gln Gly Met Ile Glu
145                 150                 155                 160

Val Ala Arg His Pro Asp Ala Val Thr Val Thr Gly Ile Val Gly
                165                 170                 175

Cys Ala Gly Leu Lys Pro Thr Val Ala Ala Ile Glu Ala Gly Lys Asp
            180                 185                 190

Ile Ala Leu Ala Asn Lys Glu Thr Leu Ile Ala Gly Gly Pro Phe Val
        195                 200                 205

Leu Pro Leu Ala Lys Lys His Asn Val Lys Ile Leu Pro Ala Asp Ser
    210                 215                 220

Glu His Ser Ala Ile Phe Gln Cys Ile Gln Gly Leu Pro Glu Gly Ala
225                 230                 235                 240

Leu Arg Arg Ile Ile Leu Thr Ala Ser Gly Gly Ala Phe Arg Asp Leu
```

-continued

```
                245                 250                 255
Pro Val Glu Lys Leu Lys Glu Val Lys Val Ala Asp Ala Leu Lys His
            260                 265                 270

Pro Asn Trp Asn Met Gly Lys Lys Ile Thr Val Asp Ser Ala Thr Leu
        275                 280                 285

Phe Asn Lys Gly Leu Glu Val Ile Glu Ala His Tyr Leu Phe Gly Ala
    290                 295                 300

Glu Tyr Asp Asp Ile Glu Ile Val Ile His Pro Gln Ser Ile Ile His
305                 310                 315                 320

Ser Met Val Glu Thr Gln Asp Ser Ser Val Leu Ala Gln Leu Gly Trp
                325                 330                 335

Pro Asp Met Arg Leu Pro Ile Leu Tyr Thr Leu Ser Trp Pro Glu Arg
            340                 345                 350

Ile Tyr Cys Ser Glu Ile Thr Trp Pro Arg Leu Asp Leu Cys Lys Val
        355                 360                 365

Asp Leu Thr Phe Lys Lys Pro Asp Asn Val Lys Tyr Pro Ser Met Asp
    370                 375                 380

Leu Ala Tyr Ala Ala Gly Arg Ala Gly Gly Thr Met Thr Gly Val Leu
385                 390                 395                 400

Ser Ala Ala Asn Glu Lys Ala Val Glu Met Phe Ile Asp Glu Lys Ile
                405                 410                 415

Gly Tyr Leu Asp Ile Phe Lys Val Val Glu Leu Thr Cys Asp Lys His
            420                 425                 430

Arg Ser Glu Met Ala Val Ser Pro Ser Leu Glu Glu Ile Val His Tyr
        435                 440                 445

Asp Gln Trp Ala Arg Asp Tyr Ala Ala Thr Val Leu Lys Ser Ala Gly
    450                 455                 460

Leu Ser Pro Ala Leu Val
465                 470

<210> SEQ ID NO 26
<211> LENGTH: 20
<212> TYPE: PRT
<213> ORGANISM: Artificial
<220> FEATURE:
<223> OTHER INFORMATION: Twenty amino acid Histidine-Tag

<400> SEQUENCE: 26

Met Gly Ser Ser His His His His His His Ser Ser Gly Leu Val Pro
1               5                   10                  15

Arg Gly Ser His
            20

<210> SEQ ID NO 27
<211> LENGTH: 418
<212> TYPE: PRT
<213> ORGANISM: Artificial
<220> FEATURE:
<223> OTHER INFORMATION: His-tagged E. coli 1-deoxy-D-xylulose
      5-phosphate reductoisomerase

<400> SEQUENCE: 27

Met Gly Ser Ser His His His His His His Ser Ser Gly Leu Val Pro
1               5                   10                  15

Arg Gly Ser His Met Lys Gln Leu Thr Ile Leu Gly Ser Thr Gly Ser
            20                  25                  30

Ile Gly Cys Ser Thr Leu Asp Val Val Arg His Asn Pro Glu His Phe
        35                  40                  45
```

```
Arg Val Val Ala Leu Val Ala Gly Lys Asn Val Thr Arg Met Val Glu
         50                  55                  60

Gln Cys Leu Glu Phe Ser Pro Arg Tyr Ala Val Met Asp Asp Glu Ala
 65                  70                  75                  80

Ser Ala Lys Leu Leu Lys Thr Met Leu Gln Gln Gln Gly Ser Arg Thr
                 85                  90                  95

Glu Val Leu Ser Gly Gln Gln Ala Ala Cys Asp Met Ala Ala Leu Glu
            100                 105                 110

Asp Val Asp Gln Val Met Ala Ala Ile Val Gly Ala Ala Gly Leu Leu
            115                 120                 125

Pro Thr Leu Ala Ala Ile Arg Ala Gly Lys Thr Ile Leu Leu Ala Asn
            130                 135                 140

Lys Glu Ser Leu Val Thr Cys Gly Arg Leu Phe Met Asp Ala Val Lys
145                 150                 155                 160

Gln Ser Lys Ala Gln Leu Leu Pro Val Asp Ser Glu His Asn Ala Ile
                165                 170                 175

Phe Gln Ser Leu Pro Gln Pro Ile Gln His Asn Leu Gly Tyr Ala Asp
                180                 185                 190

Leu Glu Gln Asn Gly Val Val Ser Ile Leu Leu Thr Gly Ser Gly Gly
            195                 200                 205

Pro Phe Arg Glu Thr Pro Leu Arg Asp Leu Ala Thr Met Thr Pro Asp
210                 215                 220

Gln Ala Cys Arg His Pro Asn Trp Ser Met Gly Arg Lys Ile Ser Val
225                 230                 235                 240

Asp Ser Ala Thr Met Met Asn Lys Gly Leu Glu Tyr Ile Glu Ala Arg
                245                 250                 255

Trp Leu Phe Asn Ala Ser Ala Ser Gln Met Glu Val Leu Ile His Pro
                260                 265                 270

Gln Ser Val Ile His Ser Met Val Arg Tyr Gln Asp Gly Ser Val Leu
                275                 280                 285

Ala Gln Leu Gly Glu Pro Asp Met Arg Thr Pro Ile Ala His Thr Met
            290                 295                 300

Ala Trp Pro Asn Arg Val Asn Ser Gly Val Lys Pro Leu Asp Phe Cys
305                 310                 315                 320

Lys Leu Ser Ala Leu Thr Phe Ala Ala Pro Asp Tyr Asp Arg Tyr Pro
                325                 330                 335

Cys Leu Lys Leu Ala Met Glu Ala Phe Glu Gln Gly Gln Ala Ala Thr
                340                 345                 350

Thr Ala Leu Asn Ala Ala Asn Glu Ile Thr Val Ala Ala Phe Leu Ala
            355                 360                 365

Gln Gln Ile Arg Phe Thr Asp Ile Ala Ala Leu Asn Leu Ser Val Leu
            370                 375                 380

Glu Lys Met Asp Met Arg Glu Pro Gln Cys Val Asp Asp Val Leu Ser
385                 390                 395                 400

Val Asp Ala Ser Ala Arg Glu Val Ala Arg Lys Glu Val Met Arg Leu
                405                 410                 415

Ala Ser

<210> SEQ ID NO 28
<211> LENGTH: 414
<212> TYPE: PRT
<213> ORGANISM: Artificial
<220> FEATURE:
<223> OTHER INFORMATION: His-tagged Synechocystis 1-deoxy-D-xylulose
      5-phosphate reductoisomerase
```

<400> SEQUENCE: 28

| | | | | | | | | | | | | | | |
|---|---|---|---|---|---|---|---|---|---|---|---|---|---|---|
|Met|Gly|Ser|Ser|His|His|His|His|His|Ser|Ser|Gly|Leu|Val|Pro|
|1| | | |5| | | | |10| | | | |15|
|Arg|Gly|Ser|His|Met|Val|Lys|Arg|Ile|Ser|Ile|Leu|Gly|Ser|Thr|Gly|
| | | |20| | | |25| | | |30| | | |
|Ser|Ile|Gly|Thr|Gln|Thr|Leu|Asp|Ile|Val|Thr|His|His|Pro|Asp|Ala|
| | |35| | | |40| | | |45| | | | |
|Phe|Gln|Val|Val|Gly|Leu|Ala|Ala|Gly|Gly|Asn|Val|Ala|Leu|Leu|Ala|
| |50| | | |55| | | |60| | | | | |
|Gln|Gln|Val|Ala|Glu|Phe|Arg|Pro|Glu|Ile|Val|Ala|Ile|Arg|Gln|Ala|
|65| | | |70| | | |75| | | |80| | |
|Glu|Lys|Leu|Glu|Asp|Leu|Lys|Ala|Ala|Val|Ala|Glu|Leu|Thr|Asp|Tyr|
| | | | |85| | | |90| | | |95| | |
|Gln|Pro|Met|Tyr|Val|Val|Gly|Glu|Glu|Val|Val|Glu|Val|Ala|Arg|
| | | |100| | | |105| | | |110| | | |
|Tyr|Gly|Asp|Ala|Glu|Ser|Val|Val|Thr|Gly|Ile|Val|Gly|Cys|Ala|Gly|
| | |115| | | |120| | | |125| | | | |
|Leu|Leu|Pro|Thr|Met|Ala|Ala|Ile|Ala|Ala|Gly|Lys|Asp|Ile|Ala|Leu|
| |130| | | |135| | | |140| | | | | |
|Ala|Asn|Lys|Glu|Thr|Leu|Ile|Ala|Gly|Ala|Pro|Val|Val|Leu|Pro|Leu|
|145| | | |150| | | |155| | | |160| | |
|Val|Glu|Lys|Met|Gly|Val|Lys|Leu|Leu|Pro|Ala|Asp|Ser|Glu|His|Ser|
| | | |165| | | |170| | | |175| | | |
|Ala|Ile|Phe|Gln|Cys|Leu|Gln|Gly|Val|Pro|Glu|Gly|Gly|Leu|Arg|Arg|
| | |180| | | |185| | | |190| | | | |
|Ile|Ile|Leu|Thr|Ala|Ser|Gly|Gly|Ala|Phe|Arg|Asp|Leu|Pro|Val|Glu|
| |195| | | |200| | | |205| | | | | |
|Arg|Leu|Pro|Phe|Val|Thr|Val|Gln|Asp|Ala|Leu|Lys|His|Pro|Asn|Trp|
|210| | | |215| | | |220| | | | | | |
|Ser|Met|Gly|Gln|Lys|Ile|Thr|Ile|Asp|Ser|Ala|Thr|Leu|Met|Asn|Lys|
|225| | | |230| | | |235| | | |240| | |
|Gly|Leu|Glu|Val|Ile|Glu|Ala|His|Tyr|Leu|Phe|Gly|Leu|Asp|Tyr|Asp|
| | | |245| | | |250| | | |255| | | |
|His|Ile|Asp|Ile|Val|Ile|His|Pro|Gln|Ser|Ile|Ile|His|Ser|Leu|Ile|
| | |260| | | |265| | | |270| | | | |
|Glu|Val|Gln|Asp|Thr|Ser|Val|Leu|Ala|Gln|Leu|Gly|Trp|Pro|Asp|Met|
| |275| | | |280| | | |285| | | | | |
|Arg|Leu|Pro|Leu|Leu|Tyr|Ala|Leu|Ser|Trp|Pro|Glu|Arg|Ile|Tyr|Thr|
|290| | | |295| | | |300| | | | | | |
|Asp|Trp|Glu|Pro|Leu|Asp|Leu|Val|Lys|Ala|Gly|Ser|Leu|Ser|Phe|Arg|
|305| | | |310| | | |315| | | |320| | |
|Glu|Pro|Asp|His|Asp|Lys|Tyr|Pro|Cys|Met|Gln|Leu|Ala|Tyr|Gly|Ala|
| | | |325| | | |330| | | |335| | | |
|Gly|Arg|Ala|Gly|Gly|Ala|Met|Pro|Ala|Val|Leu|Asn|Ala|Ala|Asn|Glu|
| | |340| | | |345| | | |350| | | | |
|Gln|Ala|Val|Ala|Leu|Phe|Leu|Gln|Glu|Lys|Ile|Ser|Phe|Leu|Asp|Ile|
| |355| | | |360| | | |365| | | | | |
|Pro|Arg|Leu|Ile|Glu|Lys|Thr|Cys|Asp|Leu|Tyr|Val|Gly|Gln|Asn|Thr|
|370| | | |375| | | |380| | | | | | |
|Ala|Ser|Pro|Asp|Leu|Glu|Thr|Ile|Leu|Ala|Ala|Asp|Gln|Trp|Ala|Arg|
|385| | | |390| | | |395| | | |400| | |
|Arg|Thr|Val|Leu|Glu|Asn|Ser|Ala|Cys|Val|Ala|Thr|Arg|Pro|
| | | | |405| | | |410| | | | | |

<210> SEQ ID NO 29
<211> LENGTH: 493
<212> TYPE: PRT
<213> ORGANISM: Artificial
<220> FEATURE:
<223> OTHER INFORMATION: His-tagged full-length rice 1-deoxy-D-xylulose 5-phosphate reductoisomerase

<400> SEQUENCE: 29

```
Met Gly Ser Ser His His His His His Ser Ser Gly Leu Val Pro
 1               5                  10                  15

Arg Gly Ser His Met Ala Leu Lys Val Val Ser Phe Pro Gly Asp Leu
                 20                  25                  30

Ala Ala Val Ser Phe Leu Asp Ser Asn Arg Gly Gly Ala Phe Asn Gln
             35                  40                  45

Leu Lys Val Asp Leu Pro Phe Gln Thr Arg Asp Arg Arg Ala Val Ser
         50                  55                  60

Leu Arg Arg Thr Cys Cys Ser Met Gln Gln Ala Pro Pro Ala Trp
 65                  70                  75                  80

Pro Gly Arg Ala Val Val Glu Pro Gly Arg Arg Ser Trp Asp Gly Pro
                 85                  90                  95

Lys Pro Ile Ser Ile Val Gly Ser Thr Gly Ser Ile Gly Thr Gln Thr
            100                 105                 110

Leu Asp Ile Val Ala Glu Asn Pro Asp Lys Phe Arg Val Val Ala Leu
        115                 120                 125

Ala Ala Gly Ser Asn Val Thr Leu Leu Ala Asp Gln Val Lys Thr Phe
    130                 135                 140

Lys Pro Lys Leu Val Ala Val Arg Asn Glu Ser Leu Val Asp Glu Leu
145                 150                 155                 160

Lys Glu Ala Leu Ala Asp Cys Asp Trp Lys Pro Glu Ile Ile Pro Gly
                165                 170                 175

Glu Gln Gly Val Ile Glu Val Ala Arg His Pro Asp Ala Val Thr Val
            180                 185                 190

Val Thr Gly Ile Val Gly Cys Ala Gly Leu Lys Pro Thr Val Ala Ala
        195                 200                 205

Ile Glu Ala Gly Lys Asp Ile Ala Leu Ala Asn Lys Glu Thr Leu Ile
    210                 215                 220

Ala Gly Gly Pro Phe Val Leu Pro Leu Ala Gln Lys His Lys Val Lys
225                 230                 235                 240

Ile Leu Pro Ala Asp Ser Glu His Ser Ala Ile Phe Gln Cys Ile Gln
                245                 250                 255

Gly Leu Pro Glu Gly Ala Leu Arg Arg Ile Ile Leu Thr Ala Ser Gly
            260                 265                 270

Gly Ala Phe Arg Asp Trp Pro Val Asp Lys Leu Lys Glu Val Lys Val
        275                 280                 285

Ala Asp Ala Leu Lys His Pro Asn Trp Asn Met Gly Lys Lys Ile Thr
    290                 295                 300

Val Asp Ser Ala Thr Leu Phe Asn Lys Gly Leu Glu Val Ile Glu Ala
305                 310                 315                 320

His Tyr Leu Phe Gly Ala Glu Tyr Asp Ile Glu Ile Val Ile His
                325                 330                 335

Pro Gln Ser Ile Ile His Ser Met Ile Glu Thr Gln Asp Ser Ser Val
            340                 345                 350

Leu Ala Gln Leu Gly Trp Pro Asp Met Arg Ile Pro Thr Leu Tyr Thr
        355                 360                 365
```

```
Met Ser Trp Pro Asp Arg Ile Tyr Cys Ser Glu Val Thr Trp Pro Arg
        370                 375                 380

Leu Asp Leu Cys Lys Leu Gly Ser Leu Thr Phe Lys Ala Pro Asp Asn
385                 390                 395                 400

Val Lys Tyr Pro Ser Met Asp Leu Ala Tyr Ala Ala Gly Arg Ala Gly
                405                 410                 415

Gly Thr Met Thr Gly Val Leu Ser Ala Ala Asn Glu Lys Ala Val Glu
                420                 425                 430

Leu Phe Ile Asp Glu Lys Ile Gly Tyr Leu Asp Ile Phe Lys Val Val
        435                 440                 445

Glu Leu Thr Cys Asp Ala His Arg Asn Glu Leu Val Thr Arg Pro Ser
        450                 455                 460

Leu Glu Glu Ile Ile His Tyr Asp Leu Trp Ala Arg Glu Tyr Ala Ala
465                 470                 475                 480

Ser Leu Gln Pro Ser Thr Gly Leu Ser Pro Val Pro Val
                485                 490

<210> SEQ ID NO 30
<211> LENGTH: 442
<212> TYPE: PRT
<213> ORGANISM: Artificial
<220> FEATURE:
<223> OTHER INFORMATION: His-tagged truncated rice 1-deoxy-D-xylulose
      5-phosphate reductoisomerase

<400> SEQUENCE: 30

Met Gly Ser Ser His His His His His His Ser Ser Gly Leu Val Pro
1               5                   10                  15

Arg Gly Ser His Met Gln Gln Ala Pro Pro Ala Trp Pro Gly Arg
                20                  25                  30

Ala Val Val Glu Pro Gly Arg Arg Ser Trp Asp Gly Pro Lys Pro Ile
                35                  40                  45

Ser Ile Val Gly Ser Thr Gly Ser Ile Gly Thr Gln Thr Leu Asp Ile
        50                  55                  60

Val Ala Glu Asn Pro Asp Lys Phe Arg Val Val Ala Leu Ala Ala Gly
65                  70                  75                  80

Ser Asn Val Thr Leu Leu Ala Asp Gln Val Lys Thr Phe Lys Pro Lys
                85                  90                  95

Leu Val Ala Val Arg Asn Glu Ser Leu Val Asp Glu Leu Lys Glu Ala
                100                 105                 110

Leu Ala Asp Cys Asp Trp Lys Pro Glu Ile Ile Pro Gly Glu Gln Gly
        115                 120                 125

Val Ile Glu Val Ala Arg His Pro Asp Ala Val Thr Val Val Thr Gly
        130                 135                 140

Ile Val Gly Cys Ala Gly Leu Lys Pro Thr Val Ala Ala Ile Glu Ala
145                 150                 155                 160

Gly Lys Asp Ile Ala Leu Ala Asn Lys Glu Thr Leu Ile Ala Gly Gly
                165                 170                 175

Pro Phe Val Leu Pro Leu Ala Gln Lys His Lys Val Lys Ile Leu Pro
                180                 185                 190

Ala Asp Ser Glu His Ser Ala Ile Phe Gln Cys Ile Gln Gly Leu Pro
        195                 200                 205

Glu Gly Ala Leu Arg Arg Ile Ile Leu Thr Ala Ser Gly Gly Ala Phe
        210                 215                 220

Arg Asp Trp Pro Val Asp Lys Leu Lys Glu Val Lys Val Ala Asp Ala
225                 230                 235                 240
```

-continued

```
Leu Lys His Pro Asn Trp Asn Met Gly Lys Lys Ile Thr Val Asp Ser
            245                 250                 255

Ala Thr Leu Phe Asn Lys Gly Leu Glu Val Ile Glu Ala His Tyr Leu
        260                 265                 270

Phe Gly Ala Glu Tyr Asp Asp Ile Glu Ile Val Ile His Pro Gln Ser
    275                 280                 285

Ile Ile His Ser Met Ile Glu Thr Gln Asp Ser Ser Val Leu Ala Gln
290                 295                 300

Leu Gly Trp Pro Asp Met Arg Ile Pro Thr Leu Tyr Thr Met Ser Trp
305                 310                 315                 320

Pro Asp Arg Ile Tyr Cys Ser Glu Val Thr Trp Pro Arg Leu Asp Leu
                325                 330                 335

Cys Lys Leu Gly Ser Leu Thr Phe Lys Ala Pro Asp Asn Val Lys Tyr
            340                 345                 350

Pro Ser Met Asp Leu Ala Tyr Ala Ala Gly Arg Ala Gly Gly Thr Met
        355                 360                 365

Thr Gly Val Leu Ser Ala Ala Asn Glu Lys Ala Val Glu Leu Phe Ile
    370                 375                 380

Asp Glu Lys Ile Gly Tyr Leu Asp Ile Phe Lys Val Val Glu Leu Thr
385                 390                 395                 400

Cys Asp Ala His Arg Asn Glu Leu Val Thr Arg Pro Ser Leu Glu Glu
                405                 410                 415

Ile Ile His Tyr Asp Leu Trp Ala Arg Glu Tyr Ala Ala Ser Leu Gln
            420                 425                 430

Pro Ser Thr Gly Leu Ser Pro Val Pro Val
        435                 440
```

<210> SEQ ID NO 31
<211> LENGTH: 418
<212> TYPE: PRT
<213> ORGANISM: Artificial
<220> FEATURE:
<223> OTHER INFORMATION: His-tagged truncated rice 1-deoxy-D-xylulose
5-phosphate reductoisomerase

<400> SEQUENCE: 31

```
Met Gly Ser Ser His His His His His His Ser Ser Gly Leu Val Pro
1               5                   10                  15

Arg Gly Ser His Met Lys Pro Ile Ser Ile Val Gly Ser Thr Gly Ser
            20                  25                  30

Ile Gly Thr Gln Thr Leu Asp Ile Val Ala Glu Asn Pro Asp Lys Phe
        35                  40                  45

Arg Val Val Ala Leu Ala Ala Gly Ser Asn Val Thr Leu Leu Ala Asp
    50                  55                  60

Gln Val Lys Thr Phe Lys Pro Lys Leu Val Ala Val Arg Asn Glu Ser
65                  70                  75                  80

Leu Val Asp Glu Leu Lys Glu Ala Leu Ala Asp Cys Asp Trp Lys Pro
                85                  90                  95

Glu Ile Ile Pro Gly Glu Gln Gly Val Ile Glu Val Ala Arg His Pro
            100                 105                 110

Asp Ala Val Thr Val Val Thr Gly Ile Val Gly Cys Ala Gly Leu Lys
        115                 120                 125

Pro Thr Val Ala Ala Ile Glu Ala Gly Lys Asp Ile Ala Leu Ala Asn
    130                 135                 140

Lys Glu Thr Leu Ile Ala Gly Gly Pro Phe Val Leu Pro Leu Ala Gln
145                 150                 155                 160
```

-continued

```
Lys His Lys Val Lys Ile Leu Pro Ala Asp Ser Glu His Ser Ala Ile
            165                 170                 175

Phe Gln Cys Ile Gln Gly Leu Pro Glu Gly Ala Leu Arg Arg Ile Ile
            180                 185                 190

Leu Thr Ala Ser Gly Gly Ala Phe Arg Asp Trp Pro Val Asp Lys Leu
            195                 200                 205

Lys Glu Val Lys Val Ala Asp Ala Leu Lys His Pro Asn Trp Asn Met
            210                 215                 220

Gly Lys Lys Ile Thr Val Asp Ser Ala Thr Leu Phe Asn Lys Gly Leu
225                     230                 235                 240

Glu Val Ile Glu Ala His Tyr Leu Phe Gly Ala Glu Tyr Asp Asp Ile
            245                 250                 255

Glu Ile Val Ile His Pro Gln Ser Ile Ile His Ser Met Ile Glu Thr
            260                 265                 270

Gln Asp Ser Ser Val Leu Ala Gln Leu Gly Trp Pro Asp Met Arg Ile
            275                 280                 285

Pro Thr Leu Tyr Thr Met Ser Trp Pro Asp Arg Ile Tyr Cys Ser Glu
            290                 295                 300

Val Thr Trp Pro Arg Leu Asp Leu Cys Lys Leu Gly Ser Leu Thr Phe
305                     310                 315                 320

Lys Ala Pro Asp Asn Val Lys Tyr Pro Ser Met Asp Leu Ala Tyr Ala
                325                 330                 335

Ala Gly Arg Ala Gly Gly Thr Met Thr Gly Val Leu Ser Ala Ala Asn
                340                 345                 350

Glu Lys Ala Val Glu Leu Phe Ile Asp Glu Lys Ile Gly Tyr Leu Asp
            355                 360                 365

Ile Phe Lys Val Val Glu Leu Thr Cys Asp Ala His Arg Asn Glu Leu
            370                 375                 380

Val Thr Arg Pro Ser Leu Glu Glu Ile Ile His Tyr Asp Leu Trp Ala
385                     390                 395                 400

Arg Glu Tyr Ala Ala Ser Leu Gln Pro Ser Thr Gly Leu Ser Pro Val
                405                 410                 415

Pro Val
```